United States Patent
Bystrom et al.

(10) Patent No.: US 9,874,569 B2
(45) Date of Patent: *Jan. 23, 2018

(54) KISSPEPTIN-54 DETECTION BY TANDEM MASS SPECTROMETRY

(71) Applicant: Quest Diagnostics Investments Incorporated, Wilmington, DE (US)

(72) Inventors: Cory E. Bystrom, Ladera Ranch, CA (US); Richard E. Reitz, Henderson, NV (US)

(73) Assignee: Quest Diagnostics Investments Incorporated, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 15/443,645

(22) Filed: Feb. 27, 2017

(65) Prior Publication Data
US 2017/0176451 A1    Jun. 22, 2017

Related U.S. Application Data

(63) Continuation of application No. 14/565,805, filed on Dec. 10, 2014, now Pat. No. 9,583,322, which is a continuation of application No. 13/682,304, filed on Nov. 20, 2012, now Pat. No. 8,916,680.

(60) Provisional application No. 61/563,435, filed on Nov. 23, 2011.

(51) Int. Cl.
*A61K 38/00* (2006.01)
*C07K 5/00* (2006.01)
*C07K 7/00* (2006.01)
*C07K 16/00* (2006.01)
*C07K 17/00* (2006.01)
*G01N 33/68* (2006.01)
*H01J 49/00* (2006.01)

(52) U.S. Cl.
CPC ....... *G01N 33/6848* (2013.01); *G01N 33/689* (2013.01); *G01N 2333/705* (2013.01); *H01J 49/0031* (2013.01); *H01J 49/0036* (2013.01); *H01J 49/0045* (2013.01)

(58) Field of Classification Search
None
See application file for complete search history.

(56) References Cited

U.S. PATENT DOCUMENTS

| | | |
|---|---|---|
| 5,772,874 A | 6/1998 | Quinn et al. |
| 5,795,469 A | 8/1998 | Quinn et al. |
| 5,919,368 A | 7/1999 | Quinn et al. |
| 5,968,367 A | 10/1999 | Quinn et al. |
| 6,107,623 A | 8/2000 | Bateman et al. |
| 6,124,137 A | 9/2000 | Hutchens et al. |
| 6,204,500 B1 | 3/2001 | Whitehouse et al. |
| 6,268,144 B1 | 7/2001 | Koester |
| 8,916,680 B2 * | 12/2014 | Bystrom ............ H01J 49/0036 250/282 |
| 9,583,322 B2 * | 2/2017 | Bystrom ............ H01J 49/0036 |
| 2002/0182660 A1 * | 12/2002 | Fong ..................... C07K 16/18 435/7.93 |
| 2011/0166063 A1 * | 7/2011 | Bossard ............ A61K 47/48215 514/5.9 |

FOREIGN PATENT DOCUMENTS

| | | | |
|---|---|---|---|
| EP | 1428835 | * 6/2004 | ............ C07K 16/18 |
| JP | 2010197110 A | 9/2010 | |
| WO | 2007055362 A1 | 5/2007 | |
| WO | 2011128357 A2 | 10/2011 | |

OTHER PUBLICATIONS

Jayasena et al. Subcutaneous Injection of Kisspeptin-54 Acutely Stimulates Gonadotropin Secretion in Women with Hypothalamic Amenorrhea, But Chronic Administration Causes Tachyphylaxis. J Clin Endocrinol Metab, Nov. 2009. vol. 94, No. 11, pp. 4315-4323.*
Stahl-Zeng et al. High sensitivity Detection of Plasma Proteins by Multiple Reaction Monitoring of N-Glycosites. MCP 2007, vol. 6 No. 10, pp. 1809-1817.*
Anderson N.L., et al., "Mass Spectrometric Quantitation of Peptides and Proteins Using Stable Isotope Standards and Capture by Anti-Peptide Antibodies (SISCAPA)," Journal of Proteome Research, 2004, vol. 3 (2), pp. 235-244.
Bartolucci G., et al., "Liquid Chromatography Tandem Mass Spectrometric Quantitation of Sulfamethazine and its Metabolites: Direct Analysis of Swine Urine by Triple Quadrupole and by Ion Trap Mass Spectrometry," Rapid Communications in Mass Spectrometry, 2000, vol. 14 (11), pp. 967-973.
Bilban M., et al., "Kisspeptin-10, a KiSS-1/Metastin-Derived Decapeptide, Is a Physiological Invasion Inhibitor of Primary Human Trophoblasts," Journal of Cell Science, 2004, vol. 117 (pt 8), pp. 1319-1328.
Chan Y.M., et al., "Kisspeptin Resets the Hypothalamic GnRH Clock in Men," The Journal of Clinical Endocrinology and Metabolism, 2011, vol. 96 (6), pp. E908-E915.
Chen C.Y., et al., "Phthalate Exposure May Affect Girl Puberty via Stimulation of Kisspeptin-54 Secretion," Epidemiology, 2011, vol. 22 (1), pp. 1-17.
Dhillo W.S., et al., "Kisspeptin-54 Stimulates the Hypothalamic-Pituitary Gonadal Axis in Human Males," The Journal of Clinical Endocrinology and Metabolism, 2005, vol. 90 (12), pp. 6609-6615.
El-Aneed A., et al., "Mass Spectrometry, Review of the Basics: Electrospray, MALDI, and Commonly Used Mass Analyzers," Applied Spectroscopy Reviews, 2009, vol. 44 (3), pp. 210-230.

(Continued)

*Primary Examiner* — Marcela M Cordero Garcia
(74) *Attorney, Agent, or Firm* — Quest Diagnostics, Inc.

(57) ABSTRACT

Methods are described for measuring the amount of a kisspeptin-54-derived peptides in a sample. More specifically, mass spectrometric methods are described for detecting and quantifying a kisspeptin-54 derived peptides in a sample utilizing on-line extraction methods coupled with tandem mass spectrometric techniques.

26 Claims, 18 Drawing Sheets

(56) References Cited

OTHER PUBLICATIONS

Gutierrez-Pascual E., et al., "In Vivo and in Vitro Structure-Activity Relationships and Structural Conformation of Kisspeptin-10-Related Peptides," Molecular Pharmacology, 2009, vol. 76 (1), pp. 58-67.

Han X., et al., "Central Administration of Kisspeptin-10 Inhibits Natriuresis and Diuresis Induced by Blood Volume Expansion in Anesthetized Male Rats," Acta Pharmacologica Sinica, 2010, vol. 31 (2), pp. 145-149.

Horikoshi Y., et al., "Dramatic Elevation of Plasma Metastin Concentrations in Human Pregnancy: Metastin as a Novel Placenta-Derived Hormone in Humans," The Journal of Clinical Endocrinology and Metabolism, 2003, vol. 88 (2), pp. 914-919.

Horikoshi Y., et al., "Dramatic Elevation of Plasma Metastin Concentrations in Human Pregnancy: Metastin as a Novel Placenta-Derived Hormone in Humans," The Journal of Clinical Endocrinology and Metabolism, 2009, vol. 94 (11), pp. 4315-4323.

International Preliminary Report on Patentability for Application No. PCT/US2012/066093, dated May 27, 2014.

International Search Report and Written Opinion for Application No. PCT/US2012/066093, dated Feb. 25, 2013.

Kotani M., et al., "The Metastasis Suppressor Gene Kiss-1 Encodes Kisspeptins, the Natural Ligands of the Orphan G Protein-coupled Receptor GPR54," The Journal of Biological Chemistry, 2001, vol. 276 (37), pp. 34631-34636.

Lee Y.R., et al., "Molecular Evolution of Multiple Forms of Kisspeptins and GPR54 Receptors in Vertebrates," Neuroendocrinology, 2009, vol. 150 (6), pp. 2837-2846.

Merchant M., et al., "Recent Advancements in Surface-Enhanced Laser Desorption/Ionization—Time of Flight—Mass Spectrometry," Electrophoresis, 2000, vol. 21 (6), pp. 1164-1167.

"Metastasis-supressor KISS-1 preproprotein [Homo sapiens]—Protein-NCBI, NCBI [online], Accession: NP002247.3, Oct. 8, 2011 [retrieved Aug. 17, 2016], Internet".

Nijher G.M.K., et al., "The Effects of Kisspeptin-54 on Blood Pressure in Humans and Plasma Kisspeptin Concentrations in Hypertensive Diseases of Pregnancy," British Journal of Clinical Pharmacology, 2010, vol. 70 (5), pp. 674-681.

Non-Final Office Action dated Oct. 20, 2015 for U.S. Appl. No. 14/565,805, filed Dec. 10, 2014.

Non-Final Office Action dated Feb. 21, 2014 for U.S. Appl. No. 13/682,304, filed Nov. 20, 2012.

Non-Final Office Action dated Jan. 22, 2016 for U.S. Appl. No. 14/063,956, filed Oct. 25, 2013.

Non-Final Office Action dated Jun. 28, 2016 for U.S. Appl. No. 14/565,805, filed Dec. 10, 2014.

Polson C., et al., "Optimization of Protein Precipitation Based Upon Effectiveness of Protein Removal and Ionization Effect in Liquid Chromatography—Tandem Mass Spectrometry," Journal of Chromatography B, 2003, vol. 785 (2), pp. 263-275.

Reynolds R.M., et al., "A Role for Kisspeptins in Pregnancy: Facts and Speculations," Reproduction, 2009, vol. 138 (1), pp. 1-7.

Robb D.B., et al., "Atmospheric Pressure Photoionization: An Ionization Method for Liquid Chromatography—Mass Spectrometry," Analytical Chemistry, 2000, vol. 72 (15), pp. 3653-3659.

Senko M.W., et al., "Collisional activation of large multiply charged ions using Fourier transform mass spectrometry", Analytical Chemistry, 1994, vol. 66 (18), pp. 2801-2808.

Supplementary European Search Report for Application No. EP12851916, dated Nov. 6, 2015, 13 pages.

Szajli E., et al., "Investigating the Quantitative Nature of MALDI-TOF MS," Molecular and Cellular Proteomics, 2008, vol. 7, pp. 2410-2418.

Thurman E.M., et al., "Chromatographic-Mass Spectrometric Food Analysis for Trace Determination of Pesticide Residues," Amadeo R., et al., eds., Elsevier, 2005, Chapter 8, pp. 369-401.

Tomita K., "Structure-activity Relationship Study on GPR54 Agonists", The 34th Structure-activity relationship symposium, 2006, Article K03, 4 Pages.

Wright Jr., G.L., et al., "Proteinchip Surface Enhanced Laser Desorption/Ionization (SELDI) Mass Spectrometry: A Novel Protein Biochip Technology for Detection of Prostate Cancer Biomarkers in Complex Protein Mixtures," Prostate cancer and Prostatic Diseases, 1999, vol. 2 (5-6), pp. 264-276.

Zhang H., et al., "Elevated Expression of KiSS-1 in Placenta of Preeclampsia and Its Effect on Trophoblast," Reproductive Biology, 2011, vol. 11 (2), pp. 99-115.

Zimmer D., et al., "Comparison of Turbulent-Flow Chromatography with Automated Solid-Phase Extraction in 96-Well Plates and Liquid-Liquid Extraction Used As Plasma Sample Preparation Techniques for Liquid Chromatography—Tandem Mass Spectrometry," Journal of Chromatography A, 1999, vol. 854, pp. 23-35.

\* cited by examiner

Figure 1A

SEQ ID NO.:1

KP 1-54

GTSLSPPPESSGS(R/P)QQPGLSAPHSRQIPAPQGAVLVQREKDLPNYNWNSFGLRF-COOH

Figure 1B

SEQ ID NO.:2

KP 1-53

GTSLSPPPESSGS(R/P)QQPGLSAPHSRQIPAPQGAVLVQREKDLPNYNWNSFGLR-COOH

Figure 1C

SEQ ID NO.:3

KP 1-52

GTSLSPPPESSGS(R/P)QQPGLSAPHSRQIPAPQGAVLVQREKDLPNYNWNSFGL-COOH

KISSPEPTIN-54 DETECTION BY TANDEM MASS SPECTROMETRY

CROSS REFERENCE TO RELATED APPLICATIONS

This application is a continuation application of U.S. application Ser. No. 14/565,805, filed Dec. 10, 2014, which is a continuation application of U.S. application Ser. No. 13/682,304, filed Nov. 20, 2012, which claims the benefit under 35 U.S.C. §119(e) of U.S. Provisional Application Ser. No. 61/563,435, filed Nov. 23, 2011, each of which is incorporated by reference in its entirety into the present disclosure.

FIELD OF THE INVENTION

The invention relates to the quantitative measurement of kisspeptin-54 and kisspeptin-54-derived peptides. In a particular aspect, the invention relates to methods for quantitative measurement of kisspeptin-54 and kisspeptin-54-derived peptides by HPLC-tandem mass spectrometry.

BACKGROUND OF THE INVENTION

The following description of the background of the invention is provided simply as an aid in understanding the invention and is not admitted to describe or constitute prior art to the invention.

The kisspeptin-54 peptide is essential for sexual reproduction and it suppresses cancer metastasis. It is also known as metastin, kisspeptin 1-54, KP-54, and KiSS-1 (68-121). Kisspeptin-54 is the carboxamide fragment of residues 68-121 of the protein KISS-1, which in turn is encoded by the KiSS-1 gene. Kisspeptin-54 potently and selectively stimulates the G-protein-coupled receptor 54 (GPR54) to signal secretion of gonadotropin-releasing hormone (GnRH). Rhythmical secretions of GnRH initiate puberty, coordinate ovulation, and maintain overall reproductive function. Kisspeptin-54 is known to suppress the progression of melanomas and breast cancers. It is postulated that kisspeptin-54 suppresses metastasis by inhibiting chemotaxis and invasion of cancer cells.

Human kisspeptin-54 (CAS No: [374683-24-6]) consists of 54 amino acids with a molecular weight of about 5857.5 g/mol and a monoisotopic mass of about 5854.0 g/mol. It is a peptide amide cleavage product containing the amino acid residues from 68 to 121 of the 138 amino acid KiSS-1 protein. Other bioactive peptides that result from cleavage of KiSS-1 are kisspeptin-14 (KP-14, 41-54), kisspeptin-13 (KP-13, residues 42-54), and kisspeptin-10 (KP-10; residues 45-54).

Kisspeptin-54 has been identified using tandem mass spectrometry. See e.g., Kotani, M., et al., *J. Biol. Chem.* 2001, 276(37), 34631-6 (isolated); Dhillo, W., et al., *J. Clin Endocrinol. Metab.* 2005, 90(12), 6609-15 (synthetic). Kisspeptin-54 has been quantitated using immunoassays. See e.g., Jayasena et al., *J. Endocrinol. Metab.* 2009, 94(11), 4315-23 (measured immunoreactivity of antibody with kisspeptin-54). Among the kisspeptin peptides, only kisspeptin-10 has been reported to be purified for and subjected to quantitative mass spectrometry. Chan et al., *J. Clin. Endocrinol. Metab.*, 2011, 96(6), E908-15.

SUMMARY OF THE INVENTION

In one aspect, the present invention provides methods of determining by mass spectrometry the amount in a sample of one or more kisspeptin-54-derived peptides selected from the group consisting of kisspeptin-54, kisspeptin-53, kisspeptin-52, kisspeptin-54(R14P), kisspeptin-53(R14P), and kisspeptin-52(R14P). These methods include subjecting the sample to ionization under conditions suitable to produce one or more multiply charged kisspeptin-54-derived peptide ions detectable by mass spectrometry; determining by mass spectrometry the amount of one or more ions from each of the one or more kisspeptin-54-derived peptides; and using the amount of the determined ions to determine the amounts of the corresponding one or more kisspeptin-54-derived peptides in the sample.

In one aspect, the methods further include, prior to ionization, enriching the concentration of the kisspeptin-54-derived peptides with an antibody specific for the N-terminal portion of kisspeptin-54. In addition or alternatively, the methods further includes adding an organic solvent, such as methanol, to the sample in an amount sufficient to precipitate one or more components from said sample, so as to enrich the concentration of the kisspeptin-54-derived peptides.

In some embodiments, ions are determined from kisspeptin-54, kisspeptin-53, and kisspeptin-52. In some embodiments, ions are determined from kisspeptin-54(R14P), kisspeptin-53(R14P), and kisspeptin-52(R14P).

In some embodiments, kisspeptin-54-derived peptides from the sample are chemically modified prior to ionization.

In some embodiments, at least one of the multiply charged ions generated from the kisspeptin-54-derived peptides is selected from the group of ions with a charge consisting of 4+, 5+, 6+, or 7+.

In some embodiments, the determined kisspeptin-54-derived peptides are selected from the group consisting of kisspeptin-54, kisspeptin-53, kisspeptin-52.

In embodiments where the one or more kisspeptin-54-derived peptides comprise kisspeptin-54, multiply charged kisspeptin-54 ions may be selected from the group of ions with m/z of 1172.4±0.5, 977.2±0.5, and 837.7±0.5.

In embodiments where the one or more kisspeptin-54-derived peptides comprise kisspeptin-54(R14P), multiply charged kisspeptin-54(R14P) ions may be selected from the group of ions with m/z of 1450.5±0.5, 1160.6±0.5, and 967.3±0.5.

In embodiments where the one or more kisspeptin-54-derived peptides comprise kisspeptin-53, multiply charged kisspeptin-53 ions may be selected from the group of ions with m/z of 1143.2±0.5, 952.7±0.5, and 816.9±0.5.

In embodiments where the one or more kisspeptin-54-derived peptides comprise kisspeptin-52, multiply charged kisspeptin-52 ions may be selected from the group of ions with m/z of 1112.0±0.5, and 926.6±0.5.

In some embodiments, mass spectrometry is tandem mass spectrometry. Embodiments utilizing tandem mass spectrometry comprise fragmenting one or more of the multiply charged kisspeptin-54-derived peptide ions into kisspeptin-54-derived peptide fragment ions.

In embodiments where kisspeptin-54 is subjected to tandem mass spectrometry, multiply charged kisspeptin-54 ions with m/z of 977.2±0.5 may be fragmented into one or more ions selected from the group consisting of ions with m/z of 1083.6±0.5 and 903.1±0.5; multiply charged kisspeptin-54 ions with m/z of 837.7±0.5 may be fragmented into an ion with m/z of 977.2±0.5.

In embodiments where kisspeptin-54(R14P) is subjected to tandem mass spectrometry, multiply charged kisspeptin-54(R14P) ions with m/z of 1160.6±0.5 may be fragmented into an ion with m/z of 1071.6±0.5; multiply charged kisspeptin-54(R14P) ions with m/z of 967.3±0.5 may be fragmented into an ion with m/z of 1071.6±0.5.

In embodiments where kisspeptin-53 is subjected to tandem mass spectrometry, multiply charged kisspeptin-53 ions with m/z of 1143.2±0.5 may be fragmented into an ion with m/z of 1053.9±0.5; multiply charged kisspeptin-53 ions with m/z of 952.7±0.5 may be fragmented into one or more ions selected from the group of ions with m/z of 1054.1±0.5 and 878.5±0.5; and multiply charged kisspeptin-53 ions with m/z of 816.7±0.5 may be fragmented into an ion with m/z of 878.3±0.5.

In embodiments where kisspeptin-52 is subjected to tandem mass spectrometry, multiply charged kisspeptin-52 ions with m/z of 1112.0±0.5 may be fragmented into one or more ions selected from the group consisting of ions with m/z of 1278.2±0.5 and 1022.9; multiply charged kisspeptin-52 ions with m/z of 926.8±0.5 may be fragmented into an ion with m/z of 1022.9±0.5.

In some embodiments, a sample is subjected to one or more processing steps prior to ionization. In some embodiments, the processing steps include one or more purification steps. In some embodiments, the processing steps include adding aqueous formic acid to the sample. In some embodiments, the processing steps include adding an organic solvent, such as methanol, to the sample in an amount sufficient to precipitate one or more components from said sample; centrifuging the organic solvent-sample mixture, wherein a portion of kisspeptin-54-derived peptides from the sample remain in the supernatant; and collecting the supernatant for further processing or ionization. In some embodiments, the processing steps include applying the sample to an anion or cation exchange column under conditions suitable to retain kisspeptin-54-derived peptides on the column; eluting kisspeptin-54-derived peptides from the column; and collecting the eluted kisspeptin-54-derived peptides for further processing or ionization. In some embodiments, the processing steps include immunopurification. In some related embodiments, immunopurification comprises capture and extraction of one or more of kisspeptin-54-derived peptides using anti-kisspeptin-54-derived peptides antibodies specific for the N-terminus of kisspeptin-54. In some embodiments, the processing steps comprise solid phase extraction (SPE). In some embodiments, the processing steps comprise high performance liquid chromatography (HPLC).

In a second aspect, the invention provides methods of reducing the degradation of kisspeptin-54-derived peptides in body fluid sample from a patient. These methods include acidifying a body fluid sample, treating a body fluid sample with an agent under conditions sufficient to precipitate proteins from said body fluid sample, or both. In some embodiments, acidifying said body fluid sample comprises acidifying with aqueous formic acid. In some embodiments, the protein precipitation agent comprises an organic solvent, such as methanol. In some related embodiments, the ratio of the volume of the organic solvent to the volume of the biological sample is about 3:1.

In a third aspect, the invention provides methods of measuring degradation of kisspeptin-54 in a biological fluid sample from a patient. These methods include subjecting a body fluid sample from a patient to ionization under conditions suitable to produce one or more multiply charged ions detectable by mass spectrometry from kisspeptin-54 and one or more kisspeptin-54 derivation products selected from the group consisting of kisspeptin-53 and kisspeptin-52; determining by mass spectrometry the amount of one or more ions of kisspeptin-54 and one or more kisspeptin-54 derivation products selected from the group consisting of kisspeptin-53 and kisspeptin-52; and using the amounts of ions determined in step b to determine the amounts of kisspeptin-54 and kisspeptin-54 derivation products in the sample.

Similar methods are provided for measuring degradation of kisspeptin-54(R14P) in a biological fluid sample from a patient. These methods include subjecting a biological fluid sample from a patient to ionization under conditions suitable to produce one or more multiply charged ions detectable by mass spectrometry from kisspeptin-54(R14P) and one or more kisspeptin-54(R14P) derivation products selected from the group consisting of kisspeptin-53(R14P) and kisspeptin-52(R14P); determining by mass spectrometry the amount of one or more ions of kisspeptin-54(R14P) and one or more kisspeptin-54(R14P) derivation products selected from the group consisting of kisspeptin-53(R14P) and kisspeptin-52 (R14P); and using the amounts of ions determined in step b to determine the amounts of kisspeptin-54(R14P) and kisspeptin-54(R14P) derivation products in the sample.

In another aspect, the invention provides methods of diagnosing or predicting risk of developing preeclampsia. These methods include providing a body fluid or tissue sample obtained from a patient; subjecting the body fluid or tissue sample to one or more processing steps to generate a processed sample comprising one or more kisspeptin-54-derived peptides selected from the group consisting of kisspeptin-54, kisspeptin-53, kisspeptin-52, kisspeptin-54 (R14P), kisspeptin-53(R14P), and kisspeptin-52(R14P); subjecting the processed sample to ionization under conditions suitable to produce one or more multiply charged ions detectable by mass spectrometry; determining by mass spectrometry the amount of one or more ions from one or more kisspeptin-54-derived peptides; and using the determined ion amounts to determine the amount of kisspeptin-54 or kisspeptin-54(R14P) in the sample. In these methods, elevated kisspeptin-54 or kisspeptin-54(R14P) levels in the sample relative to normal indicate the presence of or risk of developing preeclampsia.

In another aspect, the invention provides one or more substantially isolated polypeptides with amino acid sequences consisting of the sequences identified as SEQ ID No.:2 and SEQ ID No.:3, or proline variants thereof.

In any of the methods provided herein which utilize tandem mass spectrometry, tandem mass spectrometry may be conducted by any method known in the art, including for example, multiple reaction monitoring, precursor ion scanning, or product ion scanning.

In any of the methods provided herein which utilize two or more of an extraction column, an analytical column, and an ionization source, two or more of these components may be connected in an on-line fashion to allow for automated sample processing and analysis.

In any of the methods provided herein which require ionization of a kisspeptin-54-derived peptide, mass spectrometry is preferably performed in positive ion mode. Alternatively, mass spectrometry is performed in negative ion mode. Various ionization sources, including for example atmospheric pressure chemical ionization (APCI), electrospray ionization (ESI), and heated ESI, may be used in embodiments of the present invention. In certain preferred embodiments, kisspeptin-54-derived peptides are ionized using heated ESI in positive ion mode.

In preferred embodiments of methods presented herein which determine the amount of one or more kisspeptin-54-derived peptides in a sample, a separately detectable internal standard is provided in the sample, the amount of which is also determined in the sample. In these methods, all or a portion of both the analyte(s) of interest and the internal standard present in the sample is ionized to produce a plurality of ions detectable in a mass spectrometer, and one or more ions produced from each are detected by mass spectrometry. In these embodiments, the presence or amount of ions generated from the analyte of interest may be related to the presence of amount of analyte of interest in the sample.

In other embodiments, the amount of one or more kisspeptin-54-derived peptides in a sample may be determined by comparison to one or more external reference standards. Exemplary external reference standards include blank plasma or serum spiked with a kisspeptin-54-derived peptide or an isotopically labeled variant thereof (such as isotopically labeled kisspeptin-54 and isotopically labeled kisspeptin-54(R14P)).

As used herein, unless otherwise stated, the singular forms "a," "an," and "the" include plural reference. Thus, for example, a reference to "a protein" includes a plurality of protein molecules.

As used herein, the term "kisspeptin-54-derived peptide" refers to intact kisspeptin-54 and peptide fragments whose amino acid sequence is found within the amino acid sequence of kisspeptin-54, and all polymorphs thereof. One known polymorph of kisspeptin-54 includes a proline replacement for the arginine at position 14. This polymorph is described herein as kisspeptin-54 (proline variant) or kisspeptin-54(R14P). Kisspeptin-54-derived peptides may possess one or more of the following attributes: naturally occurring, chemically synthesized, isotopically labeled, and chemically modified. Isotopic labeling and/or chemical modification may be conducted by any of several techniques known by those of skill in the art. Other exemplary kisspeptin-54 derived peptides include kisspeptin-53, kisspeptin-52, and their protein variants.

As used herein, the term "kisspeptin-54" refers to a 54 amino acid peptide with the sequence shown as SEQ ID No.:1 in FIG. 1A.

As used herein, the term "kisspeptin-53" refers to a 53 amino acid peptide with the sequence shown as SEQ ID No.:2 in FIG. 1B.

As used herein, the term "kisspeptin-52" refers to a 52 amino acid peptide with the sequence shown as SEQ ID No.:3 in FIG. 1C.

As used herein, the term "isolated" as applied to a polypeptide means a polypeptide that has been separated from components that naturally accompany it. Typically, the polypeptide is substantially isolated when it is at least 60%, by weight, free from the proteins and naturally occurring organic molecules with which it is naturally associated. The definition also extends to a polypeptide separated from its flanking amino acids (e.g., for an amino acid sequence, isolated refers to a sequence that is free from the flanking amino acids with which the sequence is naturally associated in a polypeptide). Preferably, the polypeptide is at least 75%, more preferably at least 90%, and most preferably at least 99%, by weight, isolated. An isolated polypeptide may be obtained by standard techniques, for example, by extraction from a natural source (e.g., purification from a cell or body fluid), by expression of a recombinant nucleic acid encoding the peptide; or fusion protein thereof, by chemically synthesizing the polypeptide. Purity can be measured by any appropriate method, e.g., by column chromatography, polyacrylamide gel electrophoresis, or HPLC analysis.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected parent or daughter ions by mass spectrometry. Relative reduction as this term is used does not require that any substance, present with the analyte of interest in the material to be purified, is entirely removed by purification.

As used herein, the term "immunopurification" or "immunopurify" refers to a purification procedure that utilizes antibodies, including polyclonal or monoclonal antibodies, to enrich the one or more analytes of interest Immunopurification can be performed using any of the immunopurification methods well known in the art. Often the immunopurification procedure utilizes antibodies bound, conjugated or otherwise attached to a solid support, for example a column, well, tube, gel, capsule, particle or the like Immunopurification as used herein includes without limitation procedures often referred to in the art as immunoprecipitation, as well as procedures often referred to in the art as affinity chromatography.

As used herein, the term "immunoparticle" refers to a capsule, bead, gel particle or the like that has antibodies bound, conjugated or otherwise attached to its surface (either on and/or in the particle). In certain preferred embodiments, immunoparticles are sepharose or agarose beads. In alternative preferred embodiments, immunoparticles are glass, plastic or silica beads, or silica gel.

As used herein, the term "anti-kisspeptin-54-derived peptide antibody" refers to any polyclonal or monoclonal antibody that has an affinity for a kisspeptin-54-derived peptide. In various embodiments the specificity of kisspeptin-54-derived peptide antibodies to chemical species other than the kisspeptin-54-derived peptide may vary; for example in certain preferred embodiments the anti-kisspeptin-54-derived peptide antibodies are specific for the kisspeptin-54-derived peptide and thus have little or no affinity for chemical species other than the kisspeptin-54-derived peptide, whereas in other preferred embodiments the anti-kisspeptin-54-derived peptide antibodies are non-specific and thus bind certain chemical species other than the kisspeptin-54-derived peptide.

As used herein, the term "sample" refers to any sample that may contain an analyte of interest. As used herein, the term "body fluid" means any fluid that can be isolated from the body of an individual. For example, "body fluid" may include blood, plasma, serum, bile, saliva, urine, tears, perspiration, and the like. In some preferred embodiments, the sample comprises a body fluid sample; preferably plasma or serum, from a patient.

As used herein, the term "solid phase extraction" or "SPE" refers to a process in which a chemical mixture is separated into components as a result of the affinity of components dissolved or suspended in a solution (i.e., mobile phase) for a solid through or around which the solution is passed (i.e., solid phase). In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis. SPE, including TFLC, may operate via a unitary or mixed mode mechanism. Mixed mode mechanisms utilize ion exchange and hydrophobic retention in the same column; for example, the solid phase of a mixed-mode SPE column may exhibit strong anion exchange and hydrophobic retention; or may exhibit column exhibit strong cation exchange and hydrophobic retention.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include normal phase liquid chromatography (NPLC), reverse phase liquid chromatography (RPLC), high performance liquid chromatography (HPLC), ultra high performance liquid chromatography (UHPLC), and turbulent flow liquid chromatography (TFLC) (sometimes known as high turbulence liquid chromatography (HTLC) or high throughput liquid chromatography).

As used herein, the term "high performance liquid chromatography" or "HPLC" (sometimes known as "high pressure liquid chromatography") refers to liquid chromatography in which the degree of separation is increased by forcing the mobile phase under pressure through a stationary phase, typically a densely packed column.

As used herein, the term "ultra high performance liquid chromatography" or "UHPLC" (sometimes known as "ultra high pressure liquid chromatography") refers to liquid chromatography in which the degree of separation is increased by forcing the mobile phase under high pressure through a stationary phase, typically a densely packed column with a stationary phase comprising packing particles that have an average diameter of than 2 $\mu M$.

As used herein, the term "turbulent flow liquid chromatography" or "TFLC" (sometimes known as high turbulence liquid chromatography or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., *J Chromatogr A* 854: 23-35 (1999); see also, U.S. Pat. Nos. 5,968,367, 5,919,368, 5,795,469, and 5,772,874, which further explain TFLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 50 $\mu m$. As used in this context, the term "about" means±10%.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means±10%. In a preferred embodiment the analytical column contains particles of about 5 $\mu m$ in diameter.

As used herein, the terms "on-line" and "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 1999, 2: 264-76; and Merchant and Weinberger, *Electrophoresis* 2000, 21: 1164-67.

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e g ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photoionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photoionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber. As the droplets get smaller the electrical surface charge density increases until such time that the natural repulsion between like charges causes ions as well as neutral molecules to be released. Heated ESI is similar, but includes a heat source for heating the sample while in the capillary tube.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. See, e.g., Robb et al., *Anal. Chem.* 2000, 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase. Laser desorption thermal desorption is a technique wherein a sample containing the analyte is thermally desorbed into the gas phase by a laser pulse. The laser hits the back of a specially made 96-well plate with a metal base. The laser pulse heats the base and the heat causes the sample to transfer into the gas phase. The gas phase sample is then drawn into the mass spectrometer.

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

As used herein, the term "lower limit of quantification", "lower limit of quantitation" or "LLOQ" refers to the point where measurements become quantitatively meaningful. The analyte response at this LOQ is identifiable, discrete and reproducible with a relative standard deviation (RSD %) of less than 20% and an accuracy of 85% to 115%.

As used herein, the term "limit of detection" or "LOD" is the point at which the measured value is larger than the uncertainty associated with it. The LOD is the point at which a value is beyond the uncertainty associated with its measurement and is defined as three times the RSD of the mean at the zero concentration.

As used herein, an "amount" of an analyte in a body fluid sample refers generally to an absolute value reflecting the mass of the analyte detectable in volume of sample. However, an amount also contemplates a relative amount in comparison to another analyte amount. For example, an amount of an analyte in a sample can be an amount which is greater than a control or normal level of the analyte normally present in the sample.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.5 atomic mass unit.

The summary of the invention described above is non-limiting and other features and advantages of the invention will be apparent from the following detailed description of the invention, and from the claims.

BRIEF DESCRIPTION OF THE DRAWINGS

FIGS. 1A-C show the amino acid sequences of kisspeptin-54 (SEQ ID NO.:1), kisspeptin-53 (SEQ ID NO.:2), and kisspeptin-52 (SEQ ID NO.:3), respectively, including their respective proline variants (i.e., each having the R14P substitution).

DETAILED DESCRIPTION OF THE INVENTION

Figure 2:
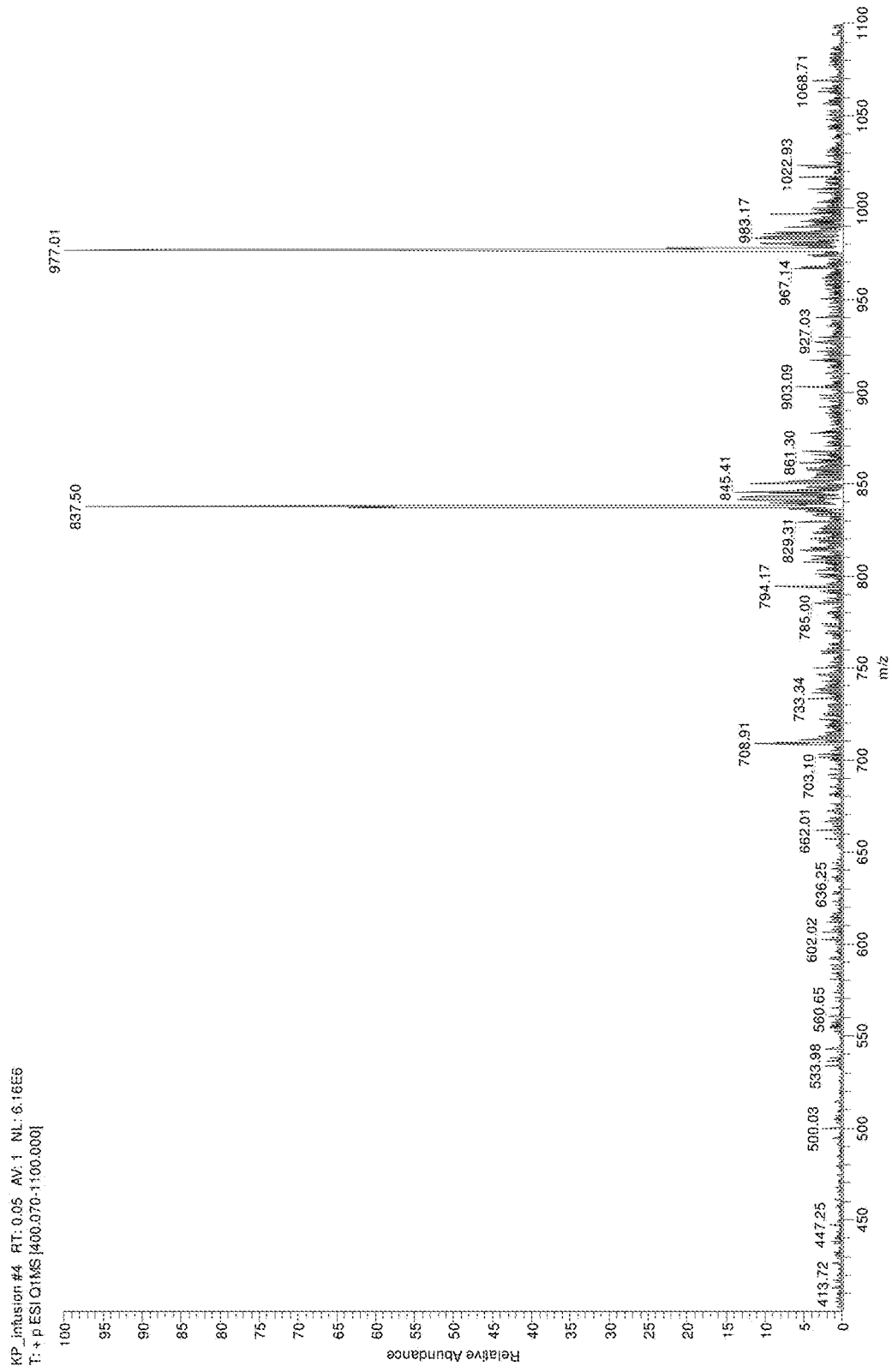
FIG. 2 shows a full scan spectrum of Kisspeptin-54. This spectrum shows generation of KP-54 [M+7H]+7 and [M+6H]+6 ions with m/z of 837.5±0.5 and 977.0±0.5, respectively. Details are discussed in Example 3.

Methods are described for measuring the amount of one or more kisspeptin-54-derived peptides in a sample. More specifically, mass spectrometric methods are described for detecting and quantifying one or more kisspeptin-54-derived peptides in a sample. The methods may utilize solid phase extraction and/or liquid chromatography, to perform a purification of selected analytes, combined with methods of mass spectrometry (MS), thereby providing a high-throughput assay system for detecting and quantifying kisspeptin-54-derived peptides in a sample. The preferred embodiments are particularly well suited for application in large clinical laboratories for automated kisspeptin-54-derived peptide quantification assay.

Suitable test samples for use in methods of the present invention include any test sample that may contain the analyte of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Preferred samples comprise bodily fluids such as blood, plasma, serum, saliva, cerebrospinal fluid, or tissue samples; preferably plasma and serum. Such samples may be obtained, for example, from a patient; that is, a living person, male or female, presenting oneself in a clinical setting for diagnosis, prognosis, or treatment of a disease or condition, such as preeclampsia. In embodiments where the sample comprises a biological sample, the methods may be used to determine the amount of one or more kisspeptin-54-derived peptides in the sample when the sample was obtained from the biological source (i.e., the amount of one or more endogenous kisspeptin-54-derived peptides in the sample).

Kisspeptin-54-derived peptides may be quantitated in patient samples from a pregnant female subject in order to diagnose or predict risk of developing preeclampsia. In diagnosing or predicting risk of preeclampsia, levels of kisspeptin-54-derived peptides from the patient sample are compared to normal levels in pregnant female samples. Elevated levels of kisspeptin-54-derived peptides in a patient sample relative to normal levels indicates the presence of or risk of developing preeclampsia.

The present invention also contemplates kits for a kisspeptin-54-derived peptide quantitation assay. A kit for a kisspeptin-54-derived peptide quantitation assay may include a kit comprising the compositions provided herein. For example, a kit may include packaging material and measured amounts of an isotopically labeled internal standard, in amounts sufficient for at least one assay. Typically, the kits will also include instructions recorded in a tangible form (e.g., contained on paper or an electronic medium) for using the packaged reagents for use in a kisspeptin-54-derived peptide quantitation assay.

Calibration and QC pools for use in embodiments of the present invention are preferably prepared using a matrix similar to the intended sample matrix, provided that the kisspeptin-54-derived peptide is essentially absent.

Sample Preparation for Mass Spectrometric Analysis

In some embodiments, samples are acidified prior to analysis. Internal standard may be added to the samples prior or subsequent to acidification.

In preparation for mass spectrometric analysis, kisspeptin-54-derived peptides may be enriched relative to one or more other components in the sample (e.g. protein) by various methods known in the art, including for example, liquid chromatography, filtration, centrifugation, thin layer chromatography (TLC), electrophoresis including capillary electrophoresis, affinity separations including immunoaffinity separations, extraction methods including ethyl acetate or methanol extraction, and the use of chaotropic agents or any combination of the above or the like.

Protein precipitation is one method of preparing a test sample, especially a biological test sample, such as serum or plasma. Protein purification methods are well known in the art, for example, Polson et al., *Journal of Chromatography B* 2003, 785:263-275, describes protein precipitation techniques suitable for use in methods of the present invention. Protein precipitation may be used to remove most of the protein from the sample leaving kisspeptin-54-derived peptides in the supernatant. The samples may be centrifuged to separate the liquid supernatant from the precipitated proteins; alternatively the samples may be filtered to remove precipitated proteins. The resultant supernatant or filtrate may then be applied directly to mass spectrometry analysis; or alternatively to further purification steps, such as liquid chromatography, and subsequent mass spectrometry analysis. In certain embodiments, the use of protein precipitation such as, for example, formic acid protein precipitation, may obviate the need for TFLC or other on-line extraction prior to mass spectrometry or HPLC and mass spectrometry.

Another method of sample purification that may be used prior to mass spectrometry is liquid chromatography (LC). Certain methods of liquid chromatography, including HPLC, rely on relatively slow, laminar flow technology. Traditional HPLC analysis relies on column packing in which laminar flow of the sample through the column is the basis for separation of the analyte of interest from the sample. The skilled artisan will understand that separation in such columns is a partition process and may select LC, including HPLC, instruments and columns that are suitable for use with kisspeptin-54-derived peptides. The chromatographic column typically includes a medium (i.e., a packing material) to facilitate separation of chemical moieties (i.e., fractionation). The medium may include minute particles. The particles typically include a bonded surface that interacts with the various chemical moieties to facilitate separation of the chemical moieties. One suitable bonded surface is a hydrophobic bonded surface such as an alkyl bonded or a cyano bonded surface. Alkyl bonded surfaces may include C-4, C-8, C-12, or C-18 bonded alkyl groups. In preferred embodiments, the column is a C-18 column. The chromatographic column includes an inlet port for receiving a sample and an outlet port for discharging an effluent that includes the fractionated sample. The sample may be supplied to the inlet port directly, or from a SPE column, such as an on-line extraction column or a TFLC column. In some embodiments, an on-line filter may be used ahead of the SPE column and or HPLC column to remove particulates and phospholipids in the samples prior to the samples reaching the SPE and/or HPLC columns. In preferred embodiments, a 0.2 µm or 0.45 µm micro-spin cellulose acetate delipidation filter is used as such an off-line filter.

In one embodiment, the sample may be applied to the LC column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytypic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one preferred embodiment, HPLC is conducted with a polar embedded analytical column chromatographic system. In certain preferred embodiments, a C-18 BEH (ethylene bridged hybrid) analytical column (e.g., an XBridge C18 BEH analytical column from Waters Inc. (2.5×50 mm, 5 µm particle size), or equivalent) is used. In certain preferred embodiments, HPLC is performed using HPLC Grade 0.2% aqueous formic acid as solvent A, and 0.2% formic acid in acetonitrile as solvent B.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In some embodiments, TFLC may be used for purification of kisspeptin-54-derived peptides prior to mass spectrometry. In such embodiments, samples may be extracted using a TFLC column which captures the analyte. The analyte is then eluted and transferred on-line to an analytical HPLC column. For example, sample extraction may be accomplished with a TFLC extraction cartridge may be accomplished with a large particle size (e.g., 25 µm or larger, such as 50 µm, particle size) packed column Sample eluted off of this column is then transferred on-line to an HPLC analytical column for further purification prior to mass spectrometry. Because the steps involved in these chromatography procedures may be linked in an automated fashion, the requirement for operator involvement during the purification of the analyte can be minimized. This feature may result in savings of time and costs, and eliminate the opportunity for operator error.

In some embodiments, the methods include immunopurifying kisspeptin-54-derived peptides prior to analysis. The immunopurification step may be performed using any of the immunopurification methods well known in the art. Often the immunopurification procedure utilizes antibodies bound, conjugated, immobilized or otherwise attached to a solid support, for example a column, well, tube, capsule, particle or the like. Generally, immunopurification methods involve (1) incubating a sample containing the analyte of interest with antibodies such that the analyte binds to the antibodies, (2) performing one or more washing steps, and (3) eluting the analyte from the antibodies.

In certain embodiments the incubation step of the immunopurification is performed with the antibodies free in solution and the antibodies are subsequently bound or attached to a solid surface prior to the washing steps. In certain embodiments this can be achieved using a primary antibody that is an anti-kisspeptin-54-derived peptide antibody and a secondary antibody attached to a solid surface that has an affinity to the primary anti-kisspeptin-54-derived peptide antibody. In alternative embodiments, the primary antibody is bound to the solid surface prior to the incubation step.

Appropriate solid supports include without limitation tubes, slides, columns, beads, capsules, particles, gels, and the like. In some preferred embodiments, the solid support is a multi-well plate, such as, for example, a 96 well plate, a 384-well plate or the like. In certain preferred embodiments the solid support are sepharose or agarose beads or gels. There are numerous methods well known in the art by which antibodies (for example, an anti-kisspeptin-54-derived peptide antibody or a secondary antibody) may be bound, attached, immobilized or coupled to a solid support, e.g., covalent or non-covalent linkages adsorption, affinity binding, ionic linkages and the like. In some embodiments antibodies are coupled using CNBr, for example the antibodies may be coupled to CNBr activated sepharose. In other embodiments, the antibody is attached to the solid support through an antibody binding protein such as protein A, protein G, protein A/G, or protein L.

The washing step of the immunopurification methods generally involve washing the solid support such that one or more kisspeptin-54-derived peptides remain bound to the anti-kisspeptin-54-derived peptide antibodies on the solid support. The elution step of the immunopurification generally involves the addition of a solution that disrupts the binding of kisspeptin-54-derived peptides to the anti-kisspeptin-54-derived peptide antibodies. Exemplary elution solutions include organic solutions (such as ethanol), salt solutions, and high or low pH solutions.

In some embodiments, immunopurification is performed using immunoparticles having anti-kisspeptin-54-derived peptide antibodies. In certain preferred embodiments the test sample possibly containing one or more kisspeptin-54-derived peptides and the immunoparticles are mixed in a tube for incubation and binding of kisspeptin-54-derived peptides to the anti-kisspeptin-54-derived peptide antibodies attached to the immunoparticles; the tube is centrifuged leaving the immunoparticles in a pellet; the supernatant is removed; the immunoparticles are washed one or more times by adding a solution to the pellet and recentrifuging; and the bound kisspeptin-54-derived peptides are eluted by adding an elution solution to the immunoparticles, the tube is centrifuged leaving the immunoparticles in a pellet; and the supernatant containing kisspeptin-54-derived peptides is collected. In related preferred embodiments, the immunopurification is performed using a column or cartridge that contains immunoparticles having anti-kisspeptin-54-derived peptide antibodies. Preferably, the such column or cartridge is configured and arranged in a manner to allow solutions to flow through while keeping the immunoparticles contained therein. In certain preferred embodiments, the solution is forced through the column or cartridge by gravity, centrifugation or pressure. The use of columns may improve the ease of performing the incubation, washing and elution steps. In some embodiments, the immunopurification may be performed by affinity chromatography; preferably automated affinity chromatography.

It has been found that kisspeptin-54 in patient samples (i.e., serum or plasma) potentially degrades at the C-terminus to form shorter kisspeptin-54-derived peptides such as KP-53 and KP-52. This degradation, if not controlled or accounted for, could result in erroneously low analytical results. For example, radioimmunoassays which rely on binding of the C-terminus of KP-54 would not account for that portion of KP-54 originally in the patient sample which has since degraded into KP-53 or KP-52. Thus, one aspect of the present invention utilizes antibodies specific for the N-terminus of kisspeptin-54-derived peptides for immunopurification and/or immunoassay. By using N-terminus specific antibodies, KP-54 and its degradation products K-53 and K-52 are captured for further analysis.

Alternatively or in addition, patient samples may be treated with one or more agents or subject to physical conditions which inhibit or prevent KP-54 degradation prior to KP-54 purification and analysis. For example, patient serum or plasma samples may be acidified, such as with formic acid, to inhibit or prevent degradation. Alternatively, patient serum or plasma samples may be subject to any protein precipitation technique known in the art (such as treatment with methanol) to inhibit or prevent degradation.

Regardless of purification methods employed and/or steps taken to reduce or inhibit KP-54 degradation, methods of analyzing patient samples may be employed which account for KP-54 degradation by simultaneously analyzing the sample for other kisspeptin-54-derived peptides. Specifically, patient samples can be simultaneously analyzed for KP-54, KP-53, and KP-52 (or their proline variants). The combined amounts of KP-54 and one or both of KP-53 and KP-52 may provide a more diagnostically useful indication of KP-54 originally present in the patient sample.

Detection and Quantitation by Mass Spectrometry

In various embodiments, kisspeptin-54-derived peptides may be ionized by any method known to the skilled artisan. Mass spectrometry is performed using a mass spectrometer, which includes an ion source for ionizing the fractionated sample and creating charged molecules for further analysis. For example ionization of the sample may be performed by electron ionization, chemical ionization, electrospray ionization (ESI), photon ionization, atmospheric pressure chemical ionization (APCI), photoionization, atmospheric pressure photoionization (APPI), Laser diode thermal desorption (LDTD), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

A kisspeptin-54-derived peptide may be ionized in positive or negative mode. In some embodiments, kisspeptin-54-derived peptides are ionized by ESI (such as by heated ESI) in positive mode.

In mass spectrometry techniques generally, after the sample has been ionized, the positively or negatively charged ions thereby created may be analyzed to determine a mass-to-charge ratio. Suitable analyzers for determining mass-to-charge ratios include quadrupole analyzers, ion traps analyzers, and time-of-flight analyzers. Exemplary ion trap methods are described in Bartolucci, et al., *Rapid Commun. Mass Spectrom.* 2000, 14:967-73.

The ions may be detected using several detection modes. For example, selected ions may be detected, i.e. using a selective ion monitoring mode (SIM), or alternatively, mass transitions resulting from collision induced dissociation or neutral loss may be monitored, e.g., multiple reaction monitoring (MRM) or selected reaction monitoring (SRM). Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

Alternate modes of operating a tandem mass spectrometric instrument include product ion scanning and precursor ion scanning. For a description of these modes of operation, see, e.g., E. Michael Thurman, et al., Chromatographic-Mass Spectrometric Food Analysis for Trace Determination of Pesticide Residues, Chapter 8 (Amadeo R. Fernandez-Alba, ed., Elsevier 2005) (387).

The results of an analyte assay may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, external standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of a kisspeptin-54-derived peptide. Methods of generating and using such standard curves are well known in the art and one of ordinary skill is capable of selecting an appropriate internal standard. For example, in preferred embodiments one or more forms of isotopically labeled kisspeptin-54-derived peptides may be used as internal standards. Numerous other methods for relating the amount of an ion to the amount of the original molecule will be well known to those of ordinary skill in the art.

As used herein, an "isotopic label" produces a mass shift in the labeled molecule relative to the unlabeled molecule when analyzed by mass spectrometric techniques. Examples of suitable labels include deuterium ($^2H$), $^{13}C$, and $^{15}N$. One or more isotopic labels can be incorporated at one or more positions in the molecule and one or more kinds of isotopic labels can be used on the same isotopically labeled molecule.

One or more steps of the methods may be performed using automated machines. In certain embodiments, one or more purification steps are performed on-line, and more preferably all of the purification and mass spectrometry steps may be performed in an on-line fashion.

In certain embodiments, such as MS/MS, where precursor ions are isolated for further fragmentation, collision activated dissociation (CAD) is often used to generate fragment ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In particularly preferred embodiments, one or more kisspeptin-54-derived peptides in a sample are detected and/or quantified using MS/MS as follows. Samples are preferably subjected to SPE, then subjected to liquid chromatography, preferably HPLC; the flow of liquid solvent from a chromatographic column enters the heated nebulizer interface of an MS/MS analyzer; and the solvent/analyte mixture is converted to vapor in the heated charged tubing of the interface. During these processes, one or more analytes (i.e., one or more kisspeptin-54-derived peptides) are analyzed. The ions, e.g. precursor ions, from a kisspeptin-54-derived peptide pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their mass to charge ratio (m/z). Quadrupole 2 (Q2) is the collision cell, where ions are fragmented. The first quadrupole of the mass spectrometer (Q1) selects for molecules with the mass to charge ratios of a kisspeptin-54-derived peptide. Precursor ions with the correct mass/charge ratios are allowed to pass into the collision chamber (Q2), while unwanted ions with any other mass/charge ratio collide with the sides of the quadrupole and are eliminated. Precursor ions entering Q2 collide with neutral argon gas molecules and fragment. The fragment ions generated are passed into quadrupole 3 (Q3), where the fragment ions of a kisspeptin-54-derived peptide are selected while other ions are eliminated. This process can be repeated as often as necessary to analyze as many kisspeptin-54-derived peptides as desired.

Using standard methods well known in the art, one of ordinary skill is capable of identifying one or more fragment ions of a particular precursor ion of a kisspeptin-54-derived peptide that may be used for selection in quadrupole 3 (Q3).

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC-MS methods. The areas under the peaks corresponding to particular ions, or the amplitude of such peaks, may be measured and correlated to the amount of the analyte of interest. In certain embodiments, the area under the curves, or amplitude of the peaks, for fragment ion(s) and/or precursor ions are measured to determine the amount of a kisspeptin-54-derived peptide. As described above, the relative abundance of a given ion may be converted into an absolute amount of the original analyte using calibration standard curves based on peaks of one or more ions of an internal molecular standard.

The following Examples serve to illustrate the invention. These Examples are in no way intended to limit the scope of the methods.

EXAMPLES

Example 1

Sample Preparation

A 100 μL serum or EDTA plasma patient sample was mixed with 300 μL of methanol containing isotope labeled kisspeptin-54 as an internal standard. The protein precipitate was removed via centrifugation and the supernatant was subjected to LC-MS and LC-MS/MS as described in the following Examples.

Example 2

Extraction of Kisspeptin-54-Derived Peptides from Samples Using Liquid Chromatography The on-line chromatographic separation of kisspeptin-54 and other kisspeptin-54-derived peptides from matrix components was performed with a Cohesive Technologies Aria TX-4 high throughput liquid chromatography (HTLC) system using Aria OS V 1.5 or newer software].

The analytes and internal standard were isolated from the serum extract using a Waters HLB C18 (2.1×20 mm, 25 μm particle size) solid phase extraction cartridge. After injection of the extract, the cartridge was washed with 90% solvent A (water+0.2% formic acid) and 10% solvent B (acetonitrile+ 0.2% formic acid). The extraction cartridge retained kisspeptin-54 while ions and very polar molecules flowed through.

The analytes were then back-flushed off the extraction cartridge over the analytical column using a pulse of 45% solvent A/55% solvent B, and 100 μL of the eluent was subjected to HPLC for analytical separation. Analytical separation was performed with a Waters X-Bridge C18 BEH analytical column (2.5×50 mm, 5 μm particle size) using a fast, multiphase gradient of increasing solvent B in solvent A. The HPLC gradient started with a 5% organic modifier which was ramped to 35% in approximately 180 seconds.

The separated analytes were then subjected to single and tandem mass spectrometry for identification and quantitation of kisspeptin-54-derived peptides.

Example 3

Detection of kisspeptin-54-Derived Peptides by MS and MS/MS

Figure 5:
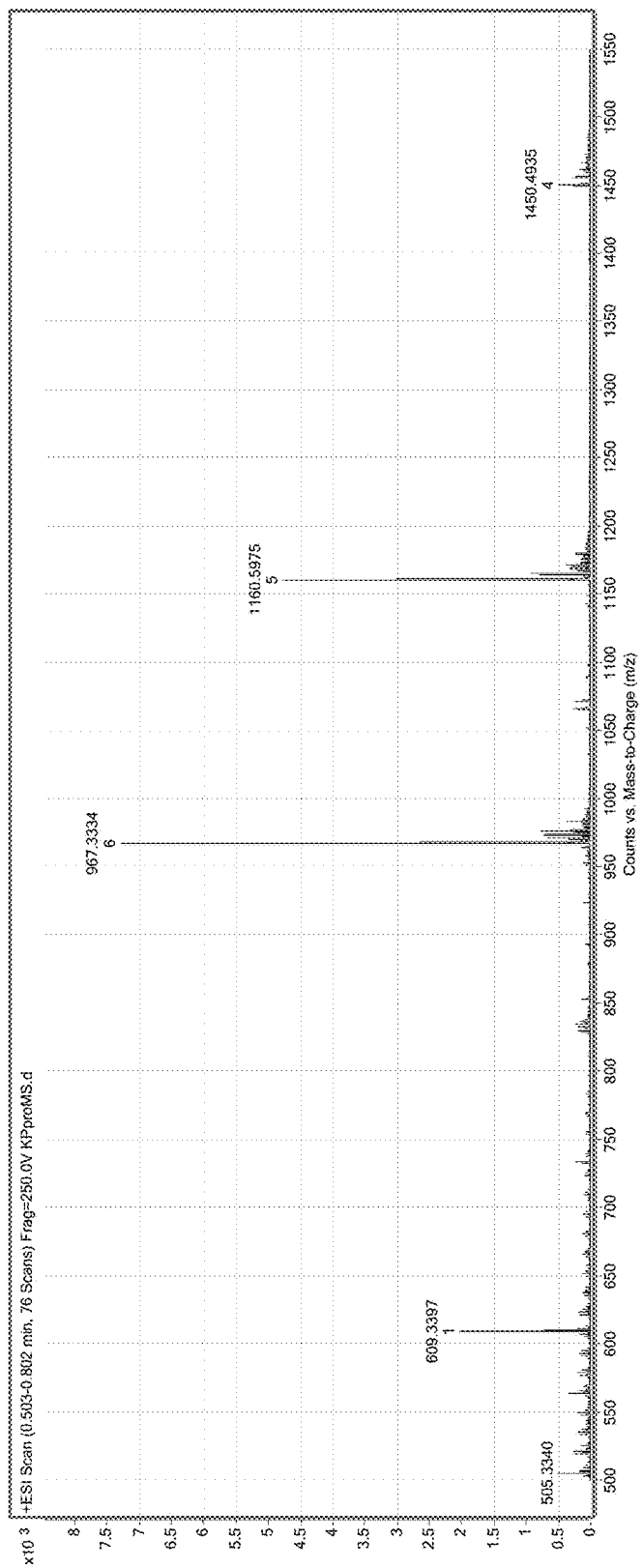
FIG. 5 shows a full scan spectrum of Kisspeptin-54 (R14P). This spectrum shows generation of KP-54(R14P) [M+6H]+6, [M+5H]+5, and [M+4H]+4 ions with m/z of 967.3±0.5, 1160.6±0.5, and 1450.5±0.5, respectively. Details are discussed in Example 3.
Figure 8:
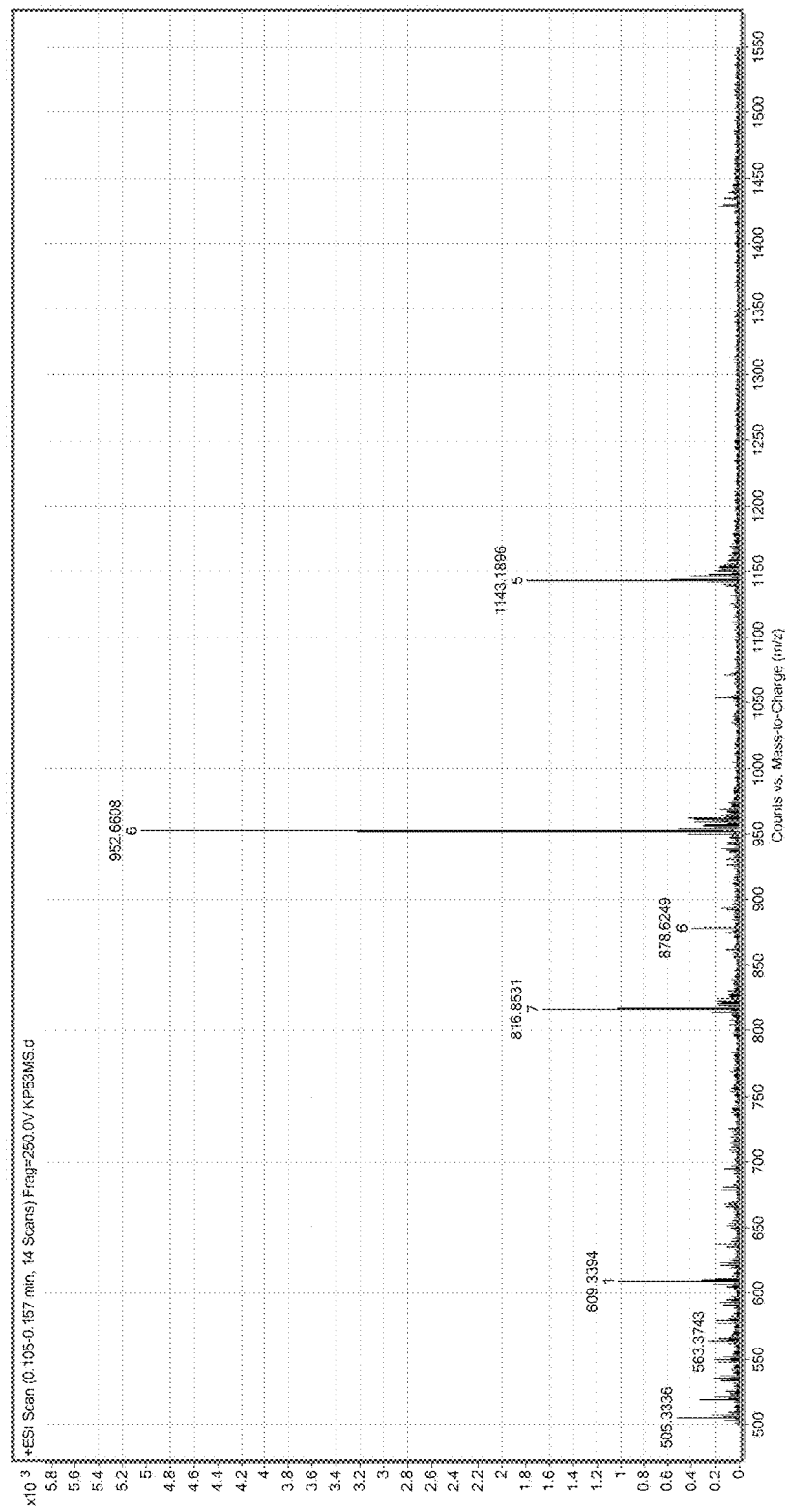
FIG. 8 shows a full scan spectrum of Kisspeptin-53. This spectrum shows generation of KP-53 [M+7H]+7, [M+6H]+6, and [M+5H]+5 ions with m/z of 816.9±0.5, 952.7±0.5, and 1143.2±0.5, respectively. Details are discussed in Example 3.
Figure 12:
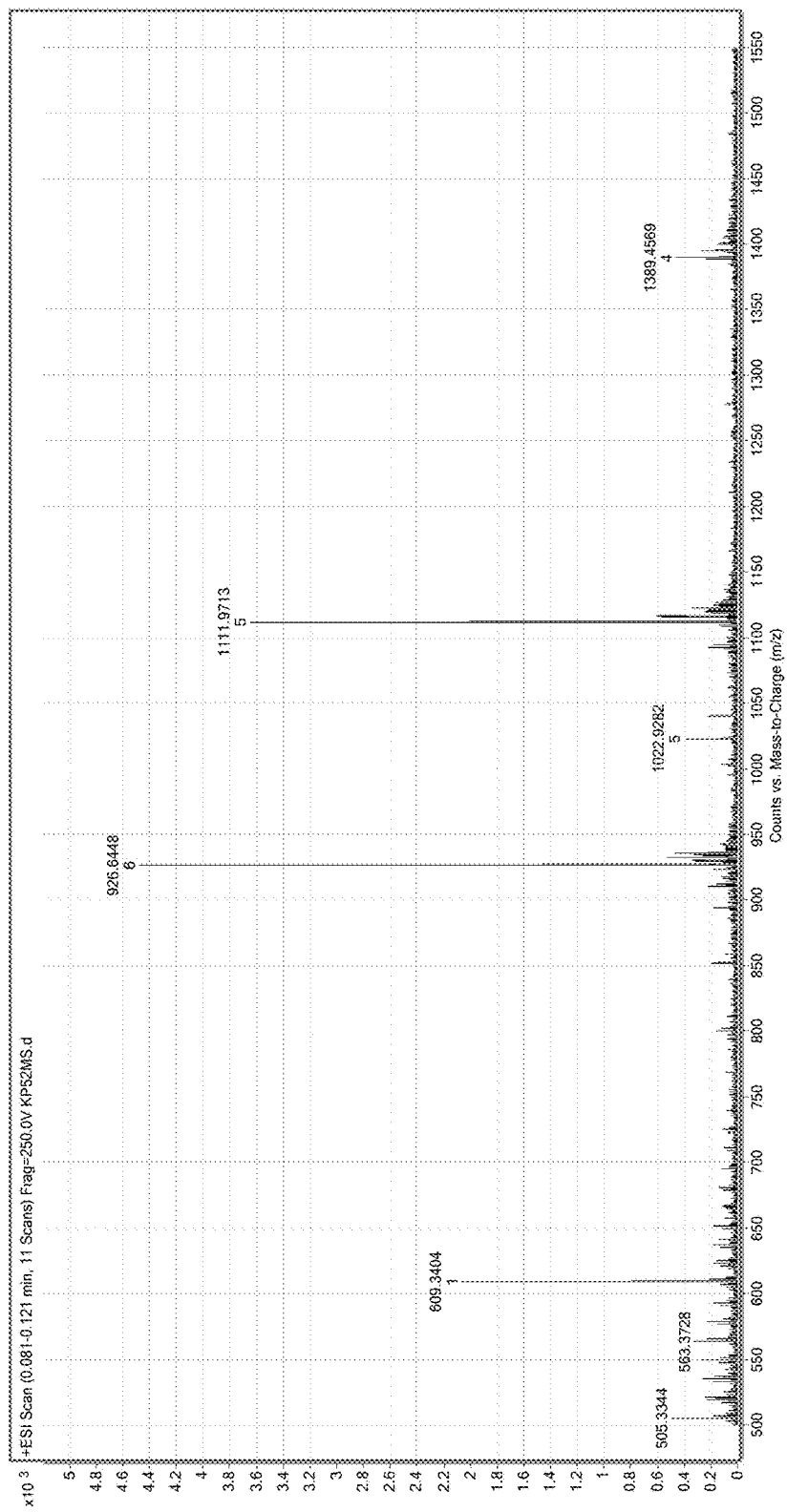
FIG. 12 shows a full scan spectrum of Kisspeptin-52. This spectrum shows generation of KP-52 [M+6H]+6, [M+5H]+5, and [M+4H]+4 ions with m/z of 926.6±0.5, 1112.0±0.5, and 1389.5±0.5, respectively. Details are discussed in Example 3.

MS was performed using a Thermo-Fisher TSQ Quantum Ultra triple quadrupole. Ionization was conducted with a heated electrospray ionization (HESI) probe. Multiply charged ions of several kisspeptin-54-derived peptides were observed. Single MS spectra showing multiply charged kisspeptin-54-related peptide ions are seen in FIG. 2 (KP-54), FIG. 5 (KP-54 (proline variant)), FIG. 8 (KP-53), and FIG. 12 (KP-52), respectively. Several major ions, several of which are seen in these figures, are compiled in Table 1.

TABLE 1

Exemplary ions observed for several Kisspeptin-54-derived peptides (positive polarity)

Figure 4:
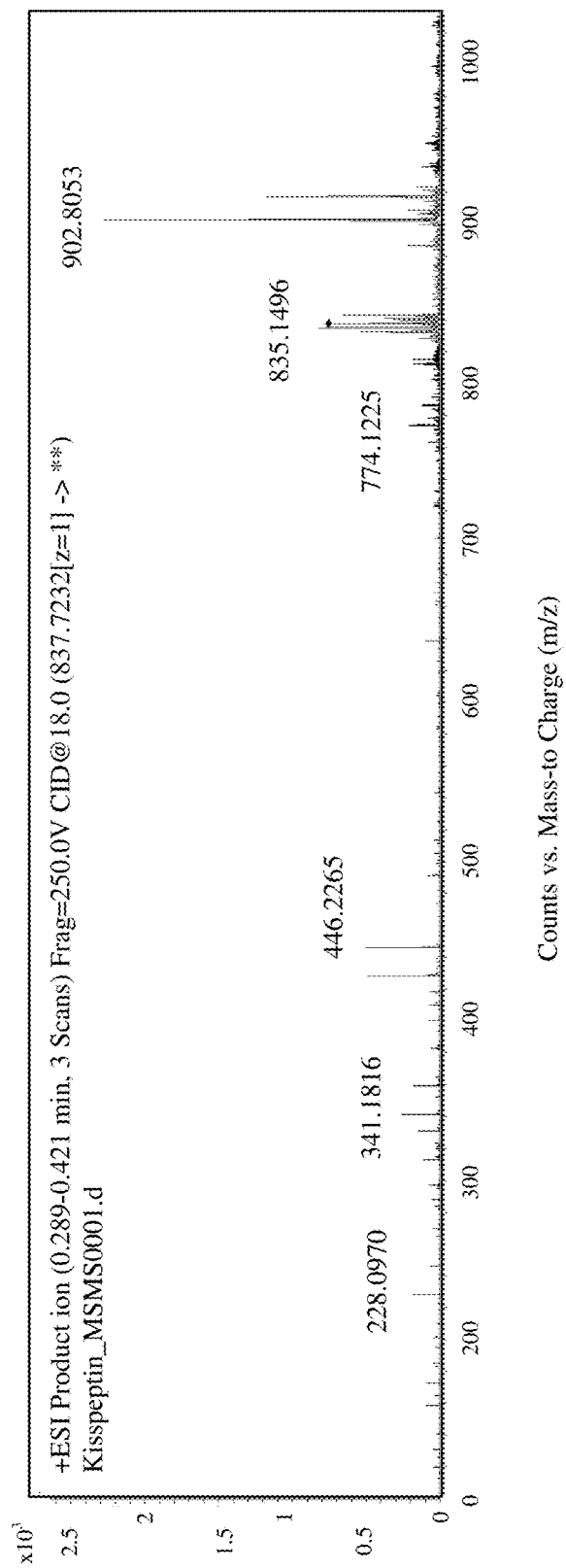
FIG. 4 shows an exemplary fragmentation spectrum of KP-54 [M+7H]+7 ion with m/z of 837.7±0.5. Exemplary fragment ions are observed at m/z of 902.8±0.5. Details are discussed in Example 3.
Figure 7:
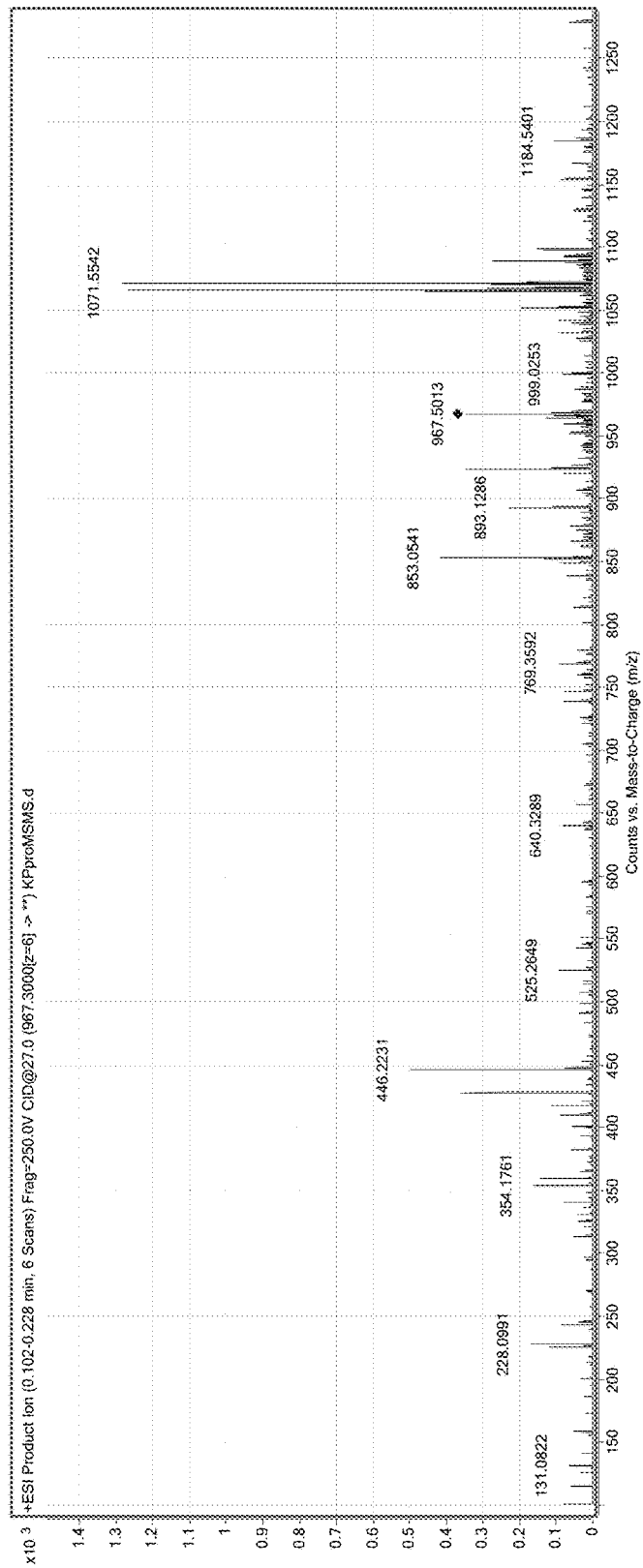
FIG. 7 shows an exemplary fragmentation spectrum of KP-54(R14P) [M+6H]+6 ion with m/z of 967.3±0.5. Exemplary fragment ions are observed at m/z of 1071.6±0.5. Details are discussed in Example 3.
Figure 11:
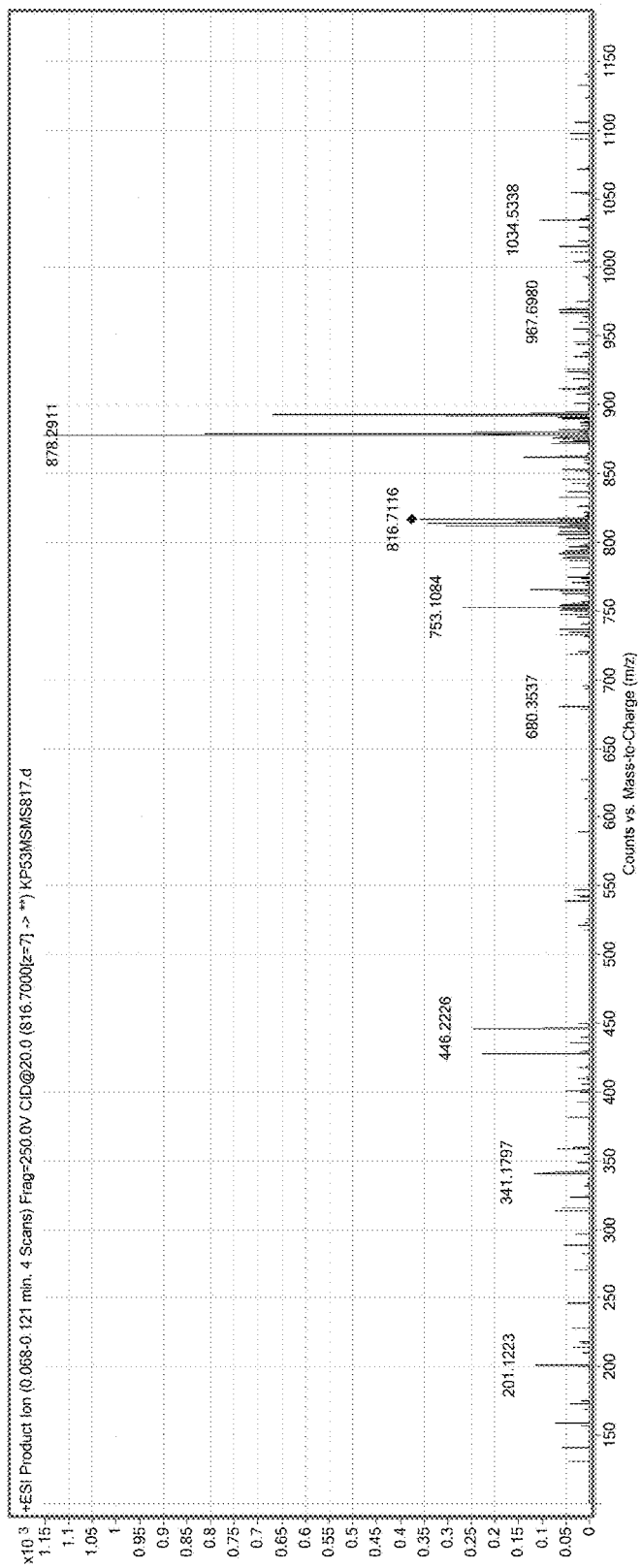
FIG. 11 shows an exemplary fragmentation spectrum of KP-53 [M+7H]+7 ion with m/z of 816.7±0.5. Exemplary fragment ions are observed at m/z of 878.3±0.5. Details are discussed in Example 3.

| Peptide | Charge state | Ion (m/z) |
| --- | --- | --- |
| KP-54 (FIG. 1) | 5+ | 1172.4 ± 0.50 |
|  | 6+ | 977.01 ± 0.50 |
|  | 7+ | 837.50 ± 0.50 |
| KP-54(R14P) (FIG. 4) | 4+ | 1450.49 ± 0.50 |
|  | 5+ | 1160.60 ± 0.50 |
|  | 6+ | 967.33 ± 0.50 |
| KP-53 (FIG. 7) | 5+ | 1143.19 ± 0.50 |
|  | 6+ | 952.66 ± 0.50 |
|  | 7+ | 816.85 ± 0.50 |
| KP-52 (FIG. 11) | 4+ | 1389.46 ± 0.50 |
|  | 5+ | 1111.97 ± 0.50 |
|  | 6+ | 926.64 ± 0.50 |

Figure 3:
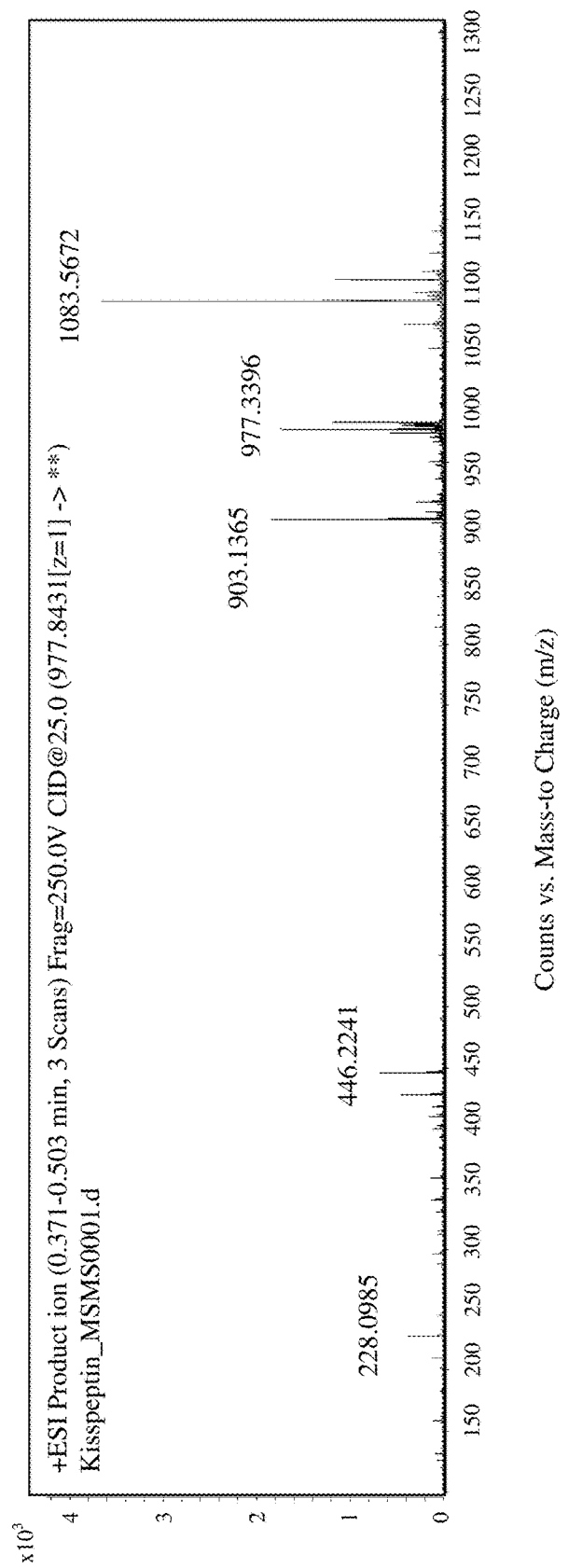
FIG. 3 shows an exemplary fragmentation spectrum of KP-54 [M+6H]+6 ion with m/z of 977.0±0.5. Exemplary fragment ions are observed at m/z of 1083.6±0.5 and 903.1±0.5. Details are discussed in Example 3.
Figure 6:
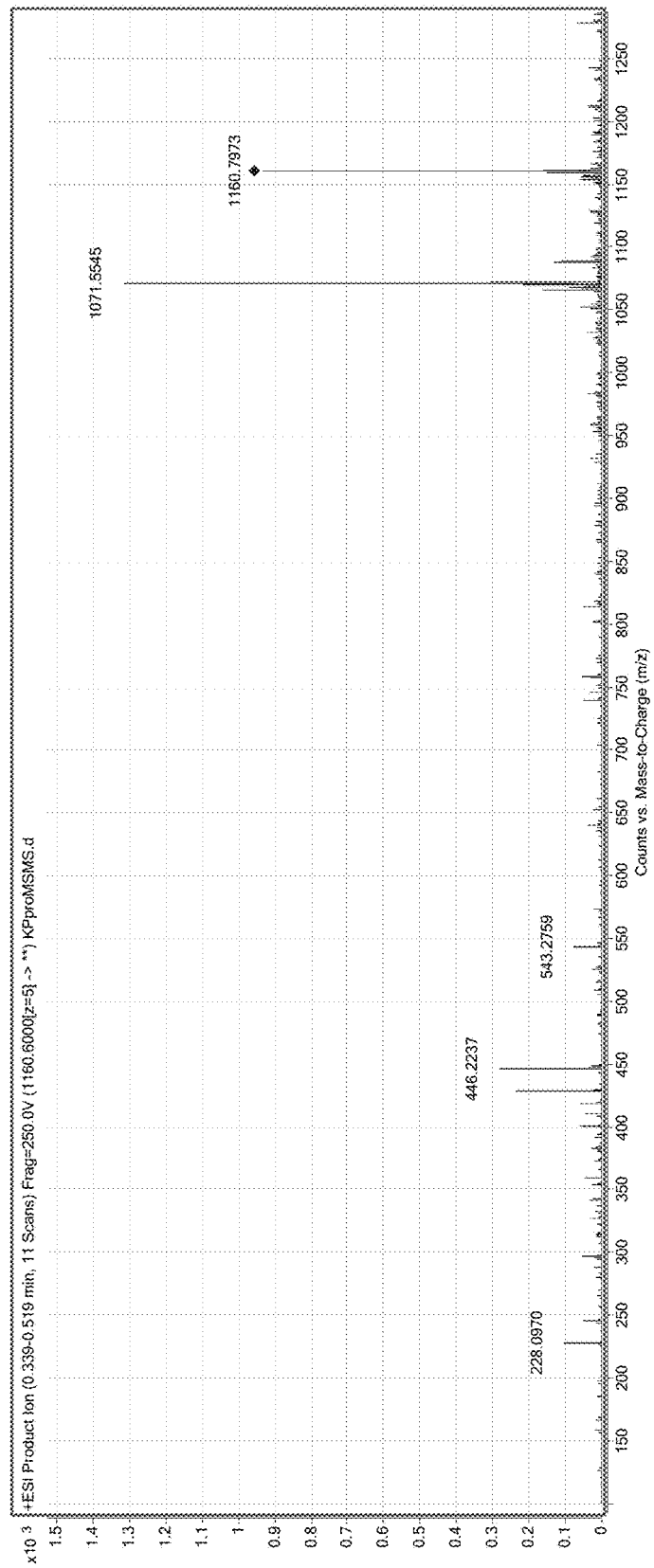
FIG. 6 shows an exemplary fragmentation spectrum of KP-54(R14P) [M+5H]+ ion with m/z of 1160.6±0.5. Exemplary fragment ions are observed at m/z of 1071.6±0.5. Details are discussed in Example 3.
Figure 9:
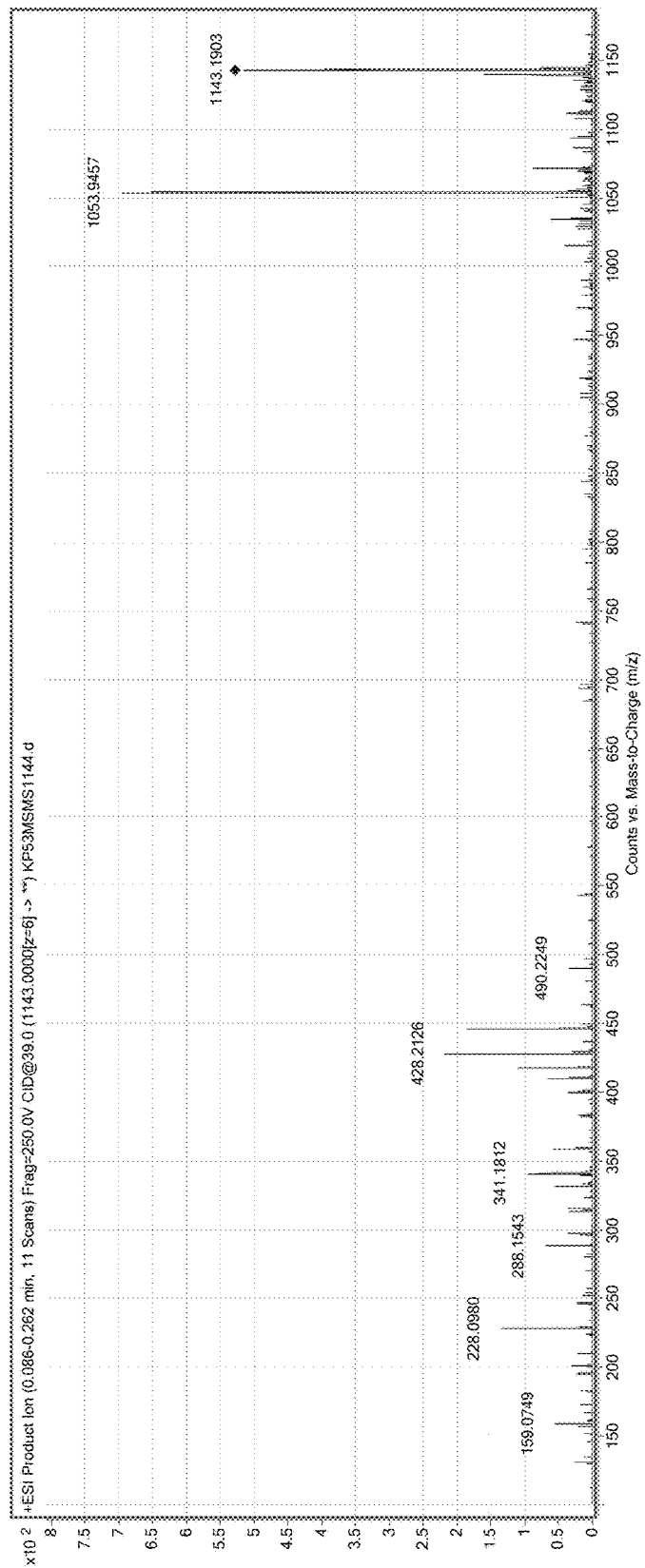
FIG. 9 shows an exemplary fragmentation spectrum of KP-53 [M+5H]+5 ion with m/z of 1143.2±0.5. Exemplary fragment ions are observed at m/z of 1053.9±0.5. Details are discussed in Example 3.
Figure 10:
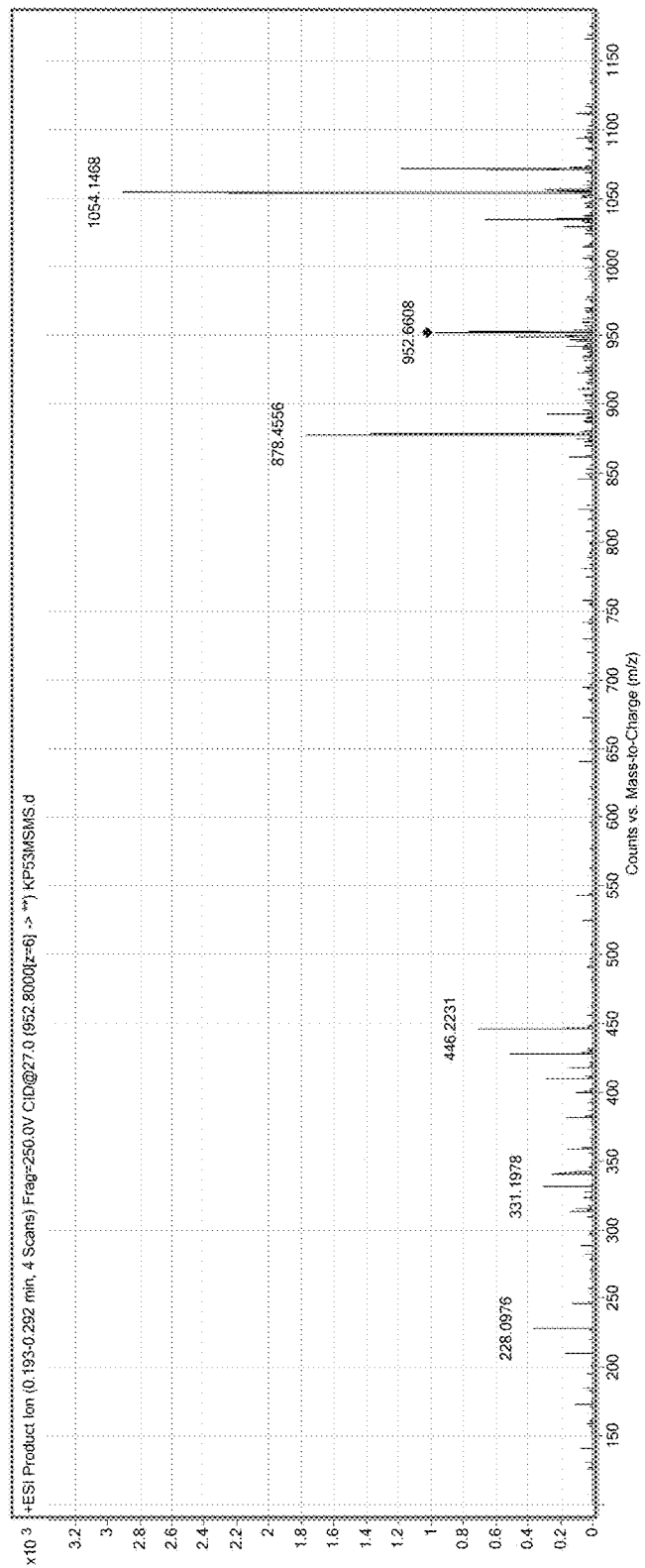
FIG. 10 shows an exemplary fragmentation spectrum of KP-53 [M+6H]+6 ion with m/z of 952.7±0.5. Exemplary fragment ions are observed at m/z of 1054.1±0.5 and 878.3±0.5. Details are discussed in Example 3.
Figure 13:
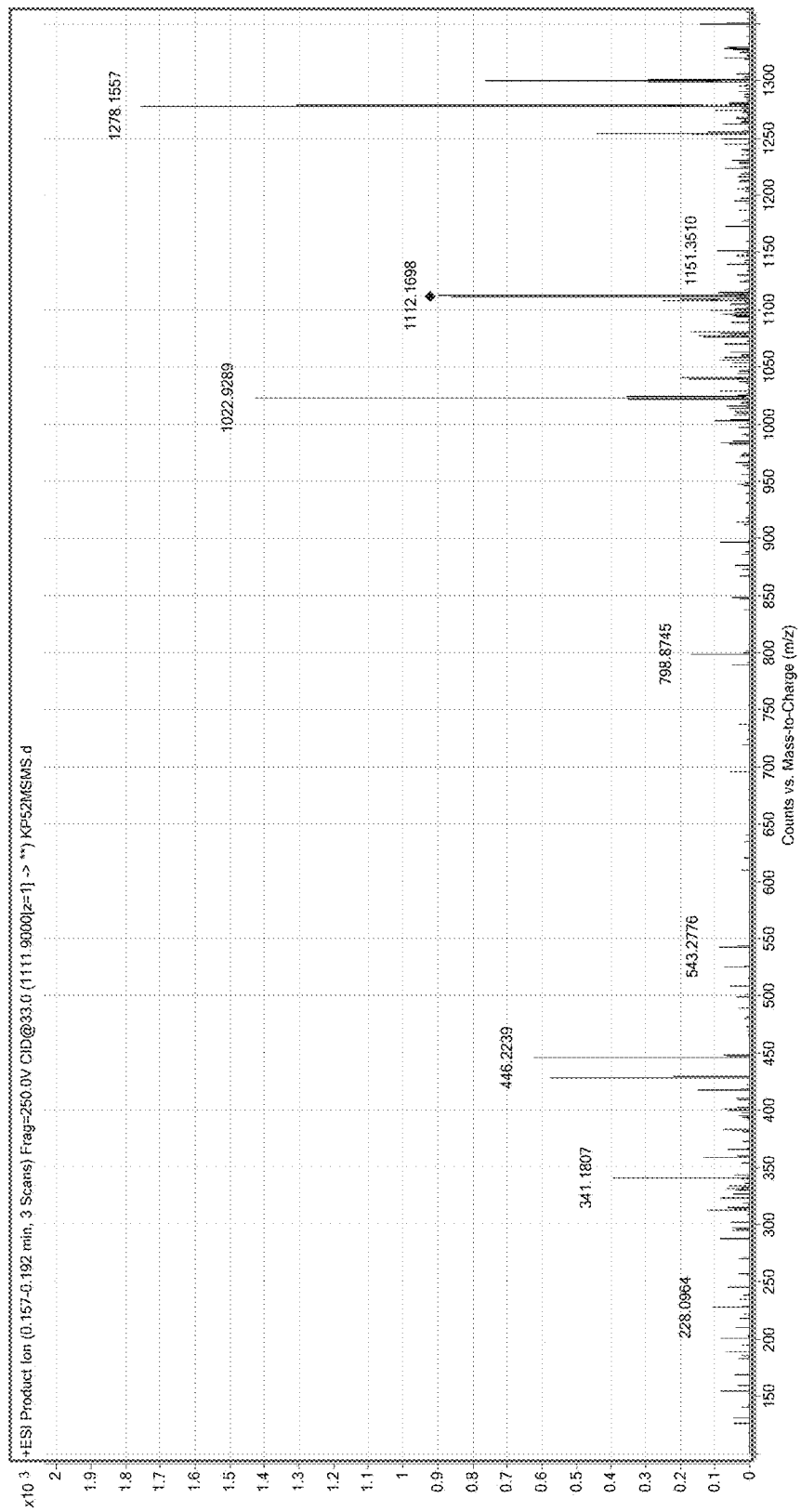
FIG. 13 shows an exemplary fragmentation spectrum of KP-52 [M+5H]+5 ion with m/z of 1111.9±0.5±0.5. Exemplary fragment ions are observed at m/z of 1278.2±0.5 and 1022.9±0.5. Details are discussed in Example 3.
Figure 14:
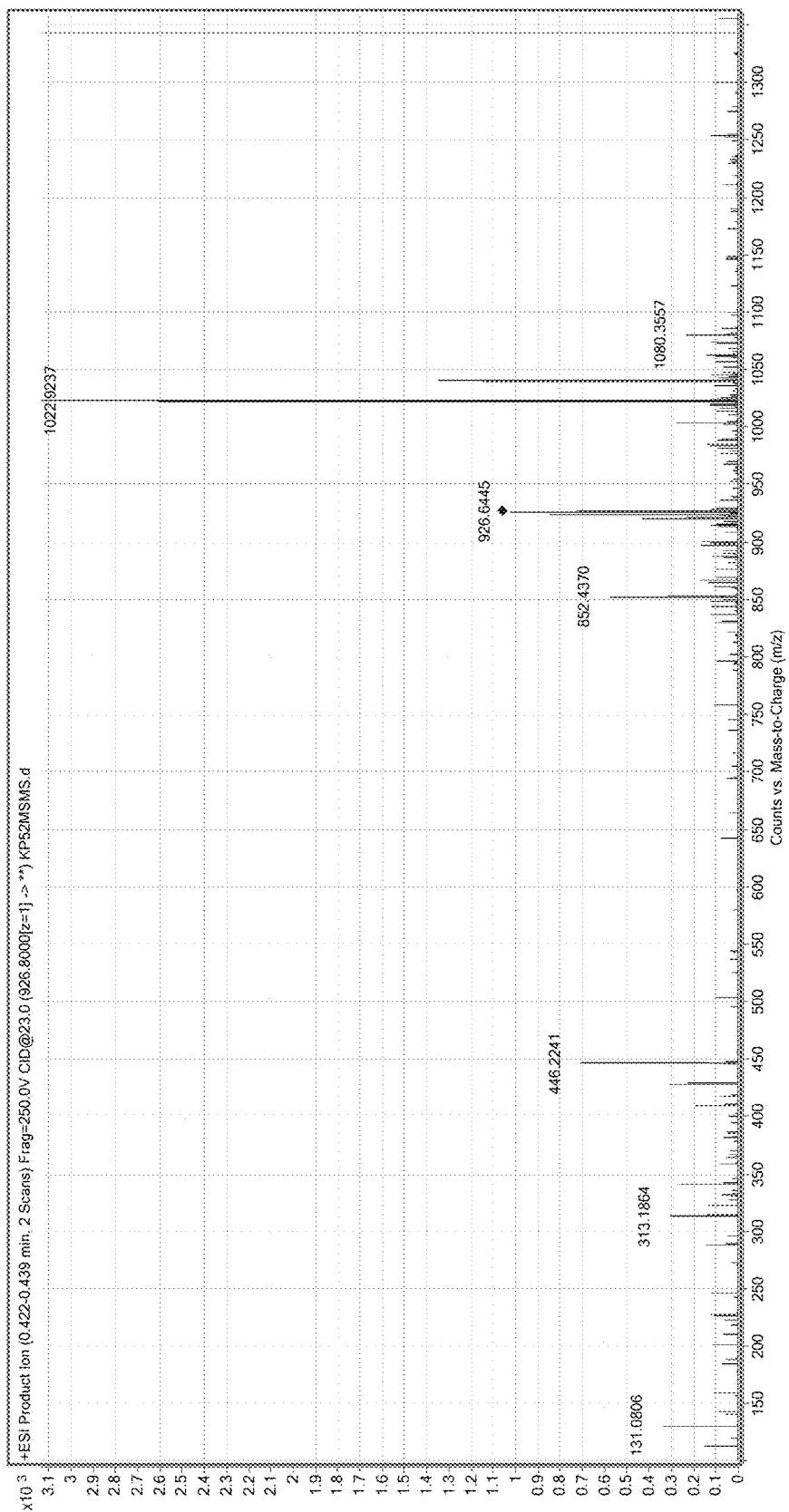
FIG. 14 shows an exemplary fragmentation spectrum of KP-52 [M+6H]+6 ion with m/z of 926.8±0.5. Exemplary fragment ions are observed at m/z of 1022.9±0.5. Details are discussed in Example 3.

Various multiply charged precursor ions from each of the above listed kisspeptin-54-derived peptides were further subjected to MS/MS resulting in a plurality of fragment ions at various charge states. For KP-54, 6+ and 7+ precursor ions were fragmented, with exemplary MS/MS spectra seen in FIGS. 3 and 4. For KP-54 (proline variant), 5+ and 6+ precursor ions were fragmented, with exemplary MS/MS spectra seen in FIGS. 6 and 7. For KP-53, 5+, 6+, and 7+ precursor ions were fragmented, with exemplary MS/MS spectra seen in FIGS. 9, 10, and 11. For KP-52, 5+ and 6+ precursor ions were fragmented, with exemplary MS/MS spectra seen in FIGS. 13 and 14. Additionally, isotopically labeled KP-54 were ionized and fragmented as discussed above (spectra not shown). The m/z ratios of several of the observed major fragment ions are compiled and listed in Table 2.

TABLE 2

Exemplary fragment ions observed for several Kisspeptin-54-derived peptides (positive polarity)

| Peptide | Precursor Ion (m/z) | Exemplary Fragment Ions (m/z) |
| --- | --- | --- |
| KP-54 | 977.0 ± 0.50 (FIG. 2) | 1083.6 ± 0.50 903.1 ± 0.50 |
|  | 837.7 ± 0.50 (FIG. 3) | 902.8 ± 0.50 |

TABLE 2-continued

Exemplary fragment ions observed for several Kisspeptin-54-derived peptides (positive polarity)

| Peptide | Precursor Ion (m/z) | Exemplary Fragment Ions (m/z) |
|---|---|---|
| KP-54(R14P) | 1160.6 ± 0.50 (FIG. 5) | 1071.6 ± 0.50 |
|  | 967.3 ± 0.50 (FIG. 6) | 1071.6 ± 0.50 |
| KP-53 | 1143.0 ± 0.50 (FIG. 8) | 1053.9 ± 0.50 |
|  | 952.8 ± 0.50 (FIG. 9) | 1054.1 ± 0.50 |
|  |  | 878.5 ± 0.50 |
|  | 816.7 ± 0.50 (FIG. 10) | 878.3 ± 0.50 |
| KP-52 | 1111.9 ± 0.50 (FIG. 12) | 1278.2 ± 0.50 |
|  |  | 1022.9 ± 0.50 |
|  | 926.8 ± 0.50 (FIG. 13) | 1022.9 ± 0.50 |

Example 4

Detection and Quantitation of Kisspeptin-54-Derived Peptides by Tandem MS

MS/MS was performed using a Thermo-Fisher TSQ Quantum Ultra triple quadrupole MS/MS system equipped with a heated electrospray ionization (HESI) probe (Thermo Electron Corporation). The following software programs, all from Thermo Electron, were used in the Examples described herein: TSQ Ultra Quantum V 1.4.1 or newer, Xcalibur V 2.0 or newer, and LCQuan V 2.5 or newer. Liquid solvent/analyte exiting the analytical column flowed to the heated nebulizer interface of the MS/MS analyzer. The solvent/analyte mixture was converted to vapor in the heated tubing of the interface. Analytes were ionized by HESI in positive polarity.

Kisspeptin-54-derived peptide ions passed to the first quadrupole (Q1), which selected KP-54 ions with a m/z of 977.0±0.5, KP-53 ions with a m/z of 952.9±0.5, KP-52 ions with a m/z of 926.9±0.5, or isotopically labeled KP-54 (IS) ions with a m/z of 980.3±0.5. Ions entering quadrupole 2 (Q2) collided with argon gas (at a collision cell energy of 28 V) to generate ion fragments, which were passed to quadrupole 3 (Q3) for further selection. The following mass transitions were used for detection and quantitation during validation on positive polarity.

TABLE 3

Exemplary mass transitions used for quantitation of kisspeptin-54-derived peptides (positive polarity)

| Analyte | Precursor Ion (m/z) | Product Ions (m/z) |
|---|---|---|
| KP 1-52 | 926.9 | 1022.9 |
| KP 1-53 | 952.9 | 1054.2 |
| KP 1-54 | 977.0 | 1083.6 |
| KP 1-54(IS) | 980.3 | 1087.3 |

The mass transitions listed in Table 3 are provided as examples only. Additional precursor/product ion pairs may be selected (for example from ions seen in FIGS. 2 to 14) to replace or augment the pairs shown in Table 3.

Figure 15:
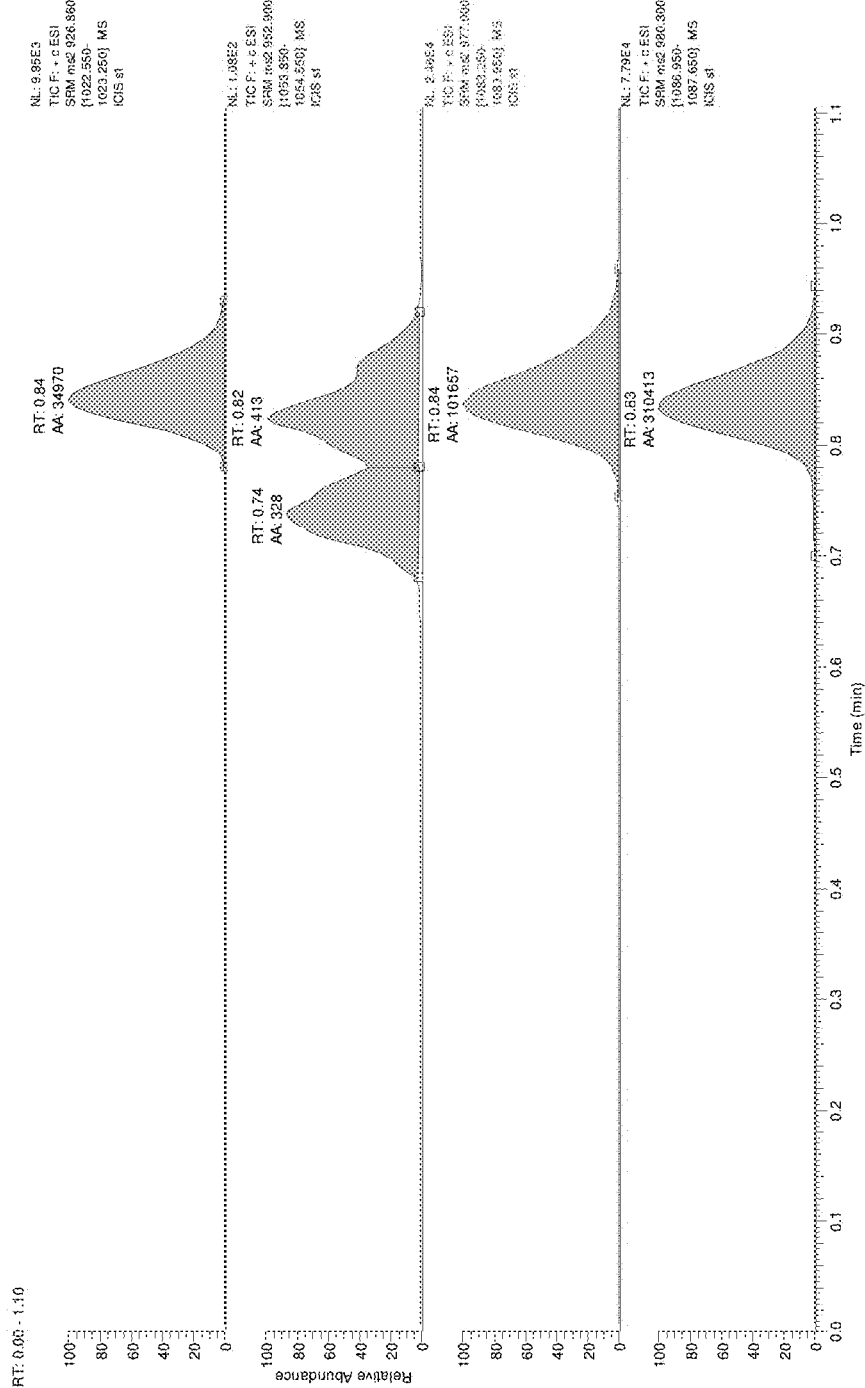
FIG. 15 shows the detection of KP-52, KP-53, KP-54, and KP-54(IS) in serum from pregnant woman #1 (28 years old, 25 weeks gestation). Details are discussed in Example 4.
Figure 16:
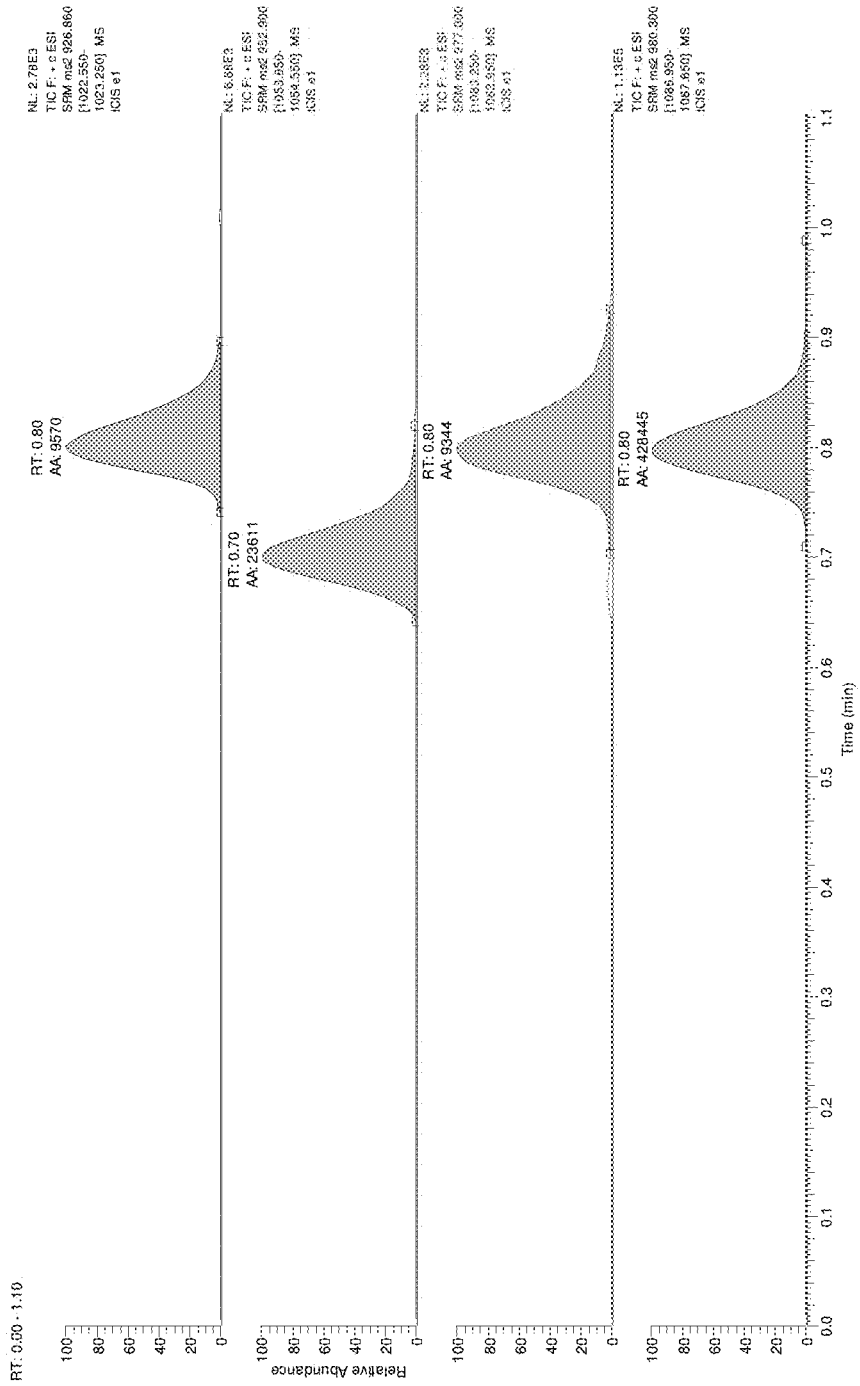
FIG. 16 shows the detection of KP-52, KP-53, KP-54, and KP-54(IS) in EDTA plasma from pregnant woman #1 (28 years old, 25 weeks gestation). Details are discussed in Example 4.
Figure 17:
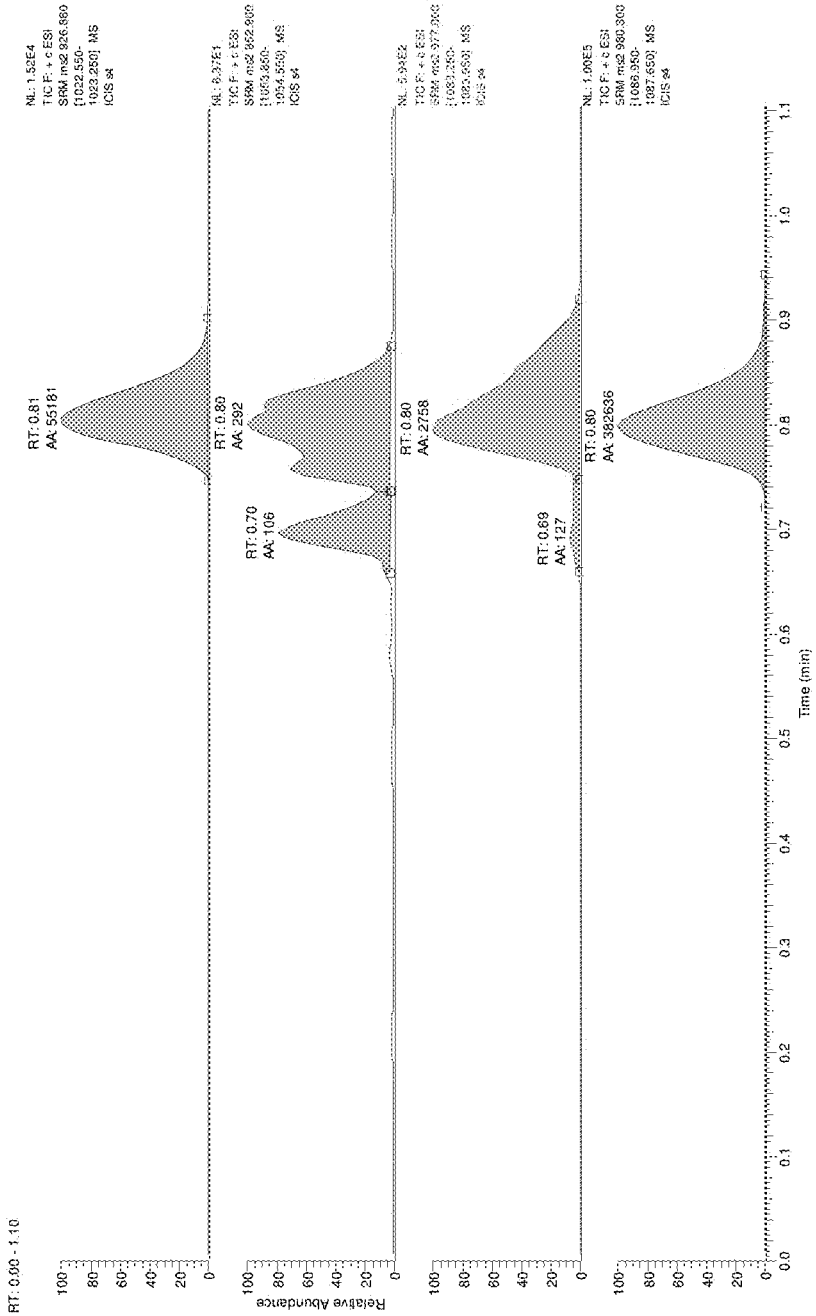
FIG. 17 shows the detection of KP-52, KP-53, KP-54, and KP-54(IS) in serum from pregnant woman #2 (21 years old, 28 weeks gestation). Details are discussed in Example 4.
Figure 18:
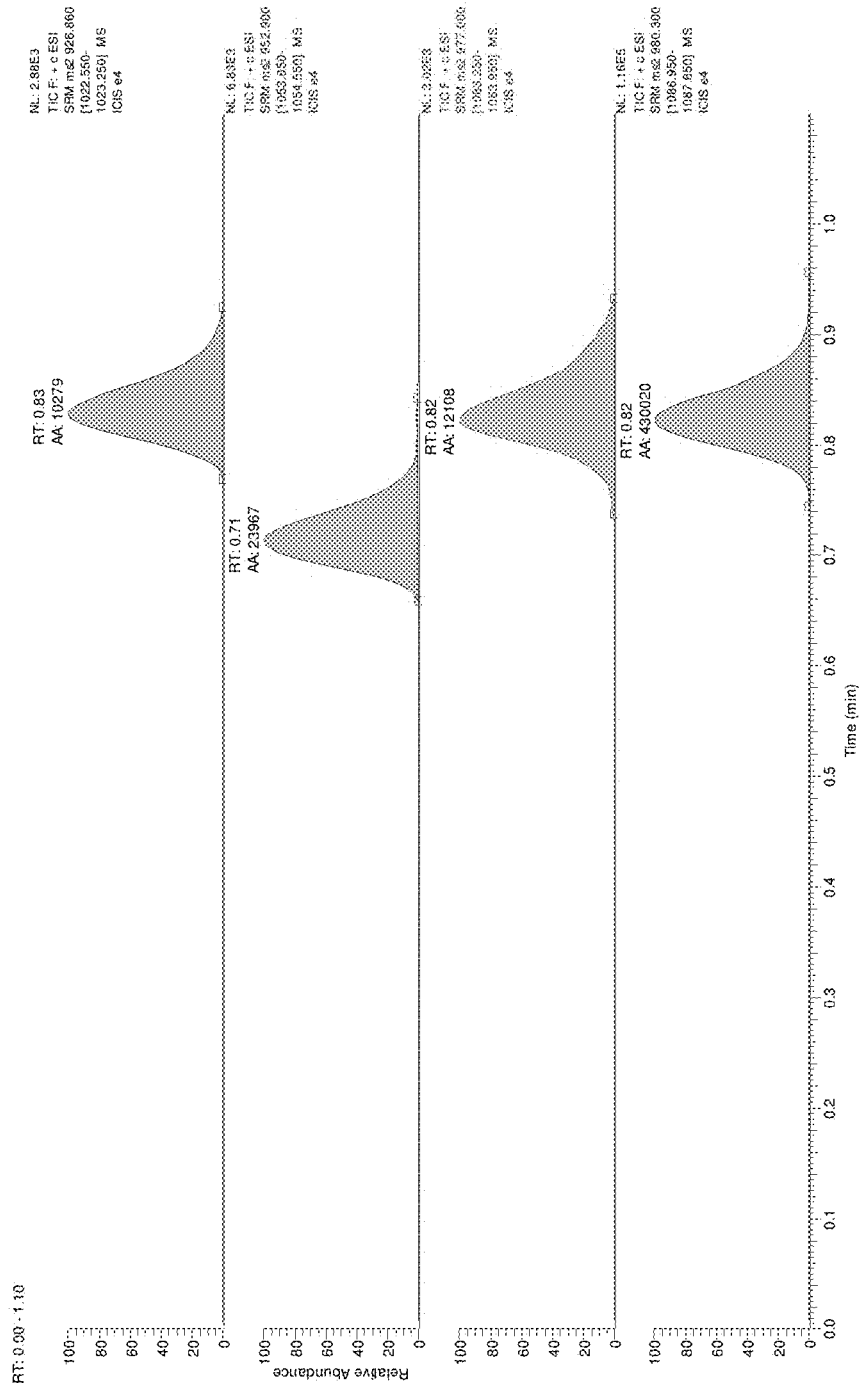
FIG. 18 shows the detection of KP-52, KP-53, KP-54, and KP-54(IS) in EDTA plasma from pregnant woman #2 (21 years old, 28 weeks gestation). Details are discussed in Example 4.

Exemplary mass chromatograms for the simultaneous quantitation of KP-52, KP-53, KP-54, and KP-54(IS) from analysis of two patient samples are shown in FIG. 15 (patient #1-28 years old, 25 weeks gestation, serum) and 16 (patient #1-28 years old, 25 weeks gestation, EDTA plasma), 17 (patient #2-21 years old, 25 weeks gestation, serum) and 18 (patient #2-21 years old, 25 weeks gestation, EDTA plasma). A comparison of the mass chromatograms from serum versus EDTA plasma samples shows that serum samples are more susceptible to formation of shorter forms of kisspeptin-54 derived peptides.

Example 5

Enrichment of Kisspeptin-54-Derived Peptides by Immunoassay

In this Example, initial patient samples are enriched by capture and extraction of kisspeptin-54-derived peptides with antibodies highly specific for the N-terminal portion of Kisspeptin.

KP-54 has been found to degrade in samples at the C-terminus, thus allowing use of N-terminal specific antibodies for capture and enrichment of kisspeptin-54-derived peptides, including KP-54, KP-53, KP-52, and isotopic and chemically modified variants thereof.

Once captured on the N-terminus specific antibody, residual sample components are washed, and the captured peptides eluted for later analysis by any method known in the art, including mass spectrometric analysis as described above.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for determining by mass spectrometry the amount in a sample of one or more kisspeptin-54-derived peptides, said method comprising:
   (a) enriching the concentration of the one or more kisspeptin-54-derived peptides in a sample with an antibody specific for the N-terminal portion of kisspeptin-54
   (b) ionizing the enriched sample to produce one or more multiply charged kisspeptin-54-derived peptide ions detectable by mass spectrometry;
   (c) determining the amount of one or more multiply charged ions selected from the group of ions with a charge consisting of 4+,5+,6+, and 7+ by mass spectrometry, wherein the amount of the ions is used to determine the amounts of the corresponding one or more kisspeptin-54-derived peptides in the sample.

2. The method in claim 1, wherein one or more kisspeptin-54-derived peptides is selected from the group consisting of kisspeptin-54, kisspeptin-53, kisspeptin-52, kisspeptin-54 (R14P), kisspeptin-53(R14P), and kisspeptin-52(R14P).

3. The method in claim 1, wherein the sample comprises two or more kisspeptin-54-derived peptides selected from the group consisting of kisspeptin-54, kisspeptin-53, kisspeptin-52, kisspeptin-54(R14P), kisspeptin-53(R14P), and kisspeptin-52(R14P).

4. The method of claim 1, wherein said one or more kisspeptin-54-derived peptides comprise kisspeptin-54, and said ions are selected from the group of ions with m/z of 1172.4±0.5, 977.2±0.5, and 837.7±0.5.

5. The method of claim 1, wherein said one or more kisspeptin-54-derived peptides comprise kisspeptin-54 (R14P), and said ions are selected from the group of ions with m/z of 1450.5±0.5, 1160.6±0.5, and 967.3±0.5.

6. The method of claim 1, wherein said one or more kisspeptin-54-derived peptides comprise kisspeptin-53 and wherein said ions are selected from the group of ions with m/z of 1143.2±0.5, 952.7±0.5, and 816.9±0.5.

7. The method of claim 1, wherein said one or more kisspeptin-54-derived peptides comprise kisspeptin-52, and said ions are selected from the group of ions with m/z of 1112.0±0.5, and 926.6±0.5.

8. The method of claim 1, wherein said mass spectrometry is tandem mass spectrometry, and said one or more ions are fragmented into kisspeptin-54-derived peptide fragment ions.

9. The method of claim 8, wherein said one or more kisspeptin-54-derived peptides comprise kisspeptin-54, said ions comprise an ion with m/z of 977.2±0.5, and said fragment ions comprise one or more ions selected from the group consisting of ions with m/z of 1083.6±0.5 and 903.1±0.5.

10. The method of claim 8, wherein said one or more kisspeptin-54-derived peptides comprise kisspeptin-54, said ions comprise an ion with m/z of 837.7±0.5, and said fragment ions comprise an ion with m/z of 902.8±0.5.

11. The method of claim 8, wherein said one or more kisspeptin-54-derived peptides comprise kisspeptin-54 (R14P), said ions comprise an ion with m/z of 1160.6±0.5, and said fragment ions comprise an ion with m/z of 1071.6±0.5.

12. The method of claim 8, wherein said one or more kisspeptin-54-derived peptides comprise kisspeptin-54 (R14P), said ions comprise an ion with m/z of 967.3±0.5, and said fragment ions comprise an ion with m/z of 1071.6±0.5.

13. The method of claim 8, wherein said one or more kisspeptin-54-derived peptides comprise kisspeptin-53, said ions comprise an ion with m/z of 1143.2±0.5, and said fragment ions comprise an ion with m/z of 1053.9±0.5.

14. The method of claim 8, wherein said one or more kisspeptin-54-derived peptides comprise kisspeptin-53, said ions comprise an ion with m/z of 952.7±0.5, and said fragment ions comprise one or more ions selected from the group consisting of ions with m/z of 1054.1±0.5 and 878.5±0.5.

15. The method of claim 8, wherein said one or more kisspeptin-54-derived peptides comprise kisspeptin-53, said ions comprise an ion with m/z of 816.7±0.5, and said fragment ions comprise an ion with m/z of 878.3±0.5.

16. The method of claim 8, wherein said one or more kisspeptin-54-derived peptides comprise kisspeptin-52, said ions comprise an ion with m/z of 1112.0±0.5, and said fragment ions comprise one or more ions selected from the group consisting of ions with m/z of 1278.2±0.5 and 1022.9±0.5.

17. The method of claim 8, wherein said one or more kisspeptin-54-derived peptides comprise kisspeptin-52, said ions comprise an ion with m/z of 926.8±0.5, and said fragment ions comprise one or more ions selected from the group consisting of ions with m/z of 1022.9±0.5.

18. The method of claim 1, further comprising adding one or more isotopically labeled kisspeptin-54-derived peptide to the sample before the ionization step.

19. The method of claim 1, further comprising subjecting the sample to acidification.

20. The method of claim 19, wherein acidifying said body fluid sample comprises acidifying with aqueous formic acid.

21. The method of claim 1, further comprising subjecting the sample to precipitation with methanol.

22. The method of claim 21, wherein said protein precipitation agent comprises methanol.

23. The method of claim 1, further comprising purifying said sample with solid phase extraction (SPE) or high performance liquid chromatography (HPLC).

24. The method of claim 1, wherein the sample comprises a biological sample.

25. The method of claim 24, wherein the biological sample comprises plasma or serum.

26. The method of claim 1, further comprising determining the total amount of kisspeptin-54 in the sample before kisspeptin-54 is degraded in the sample by summing the determined-amonun of kissepeptin-54 -derived peptides in the sample.

\* \* \* \* \*

SEQUENCE LISTING

<160> NUMBER OF SEQ ID NOS: 3

<210> SEQ ID NO 1
<211> LENGTH: 54
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Arg or Pro
<220> FEATURE:
<221> NAME/KEY: MOD_RES
<222> LOCATION: (54)..(54)
<223> OTHER INFORMATION: Phe-COOH

<400> SEQUENCE: 1

Gly Thr Ser Leu Ser Pro Pro Glu Ser Gly Ser Xaa Gln Gln
1               5                   10                  15

Pro Gly Leu Ser Ala Pro His Ser Arg Gln Ile Pro Ala Pro Gln Gly
            20                  25                  30

Ala Val Leu Val Gln Arg Glu Lys Asp Leu Pro Asn Tyr Asn Trp Asn
        35                  40                  45

Ser Phe Gly Leu Arg Phe
    50

<210> SEQ ID NO 2
<211> LENGTH: 53
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Arg or Pro
<220> FEATURE:
<221> NAME/KEY: MOD_RES
<222> LOCATION: (53)..(53)
<223> OTHER INFORMATION: Arg-COOH

<400> SEQUENCE: 2

Gly Thr Ser Leu Ser Pro Pro Glu Ser Gly Ser Xaa Gln Gln
1               5                   10                  15

Pro Gly Leu Ser Ala Pro His Ser Arg Gln Ile Pro Ala Pro Gln Gly
            20                  25                  30

Ala Val Leu Val Gln Arg Glu Lys Asp Leu Pro Asn Tyr Asn Trp Asn
        35                  40                  45

Ser Phe Gly Leu Arg
    50

<210> SEQ ID NO 3
<211> LENGTH: 52
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Arg or Pro
<220> FEATURE:
<221> NAME/KEY: MOD_RES
<222> LOCATION: (52)..(52)
<223> OTHER INFORMATION: Leu-COOH

<400> SEQUENCE: 3

Gly Thr Ser Leu Ser Pro Pro Glu Ser Gly Ser Xaa Gln Gln
1               5                   10                  15

Pro Gly Leu Ser Ala Pro His Ser Arg Gln Ile Pro Ala Pro Gln Gly
            20                  25                  30

```
Ala Val Leu Val Gln Arg Glu Lys Asp Leu Pro Asn Tyr Asn Trp Asn
        35                  40                  45
Ser Phe Gly Leu
    50
```